US008667054B2

(12) United States Patent
Tahan

(10) Patent No.: US 8,667,054 B2
(45) Date of Patent: *Mar. 4, 2014

(54) SYSTEMS AND METHODS FOR NETWORKED, IN-CONTEXT, COMPOSED, HIGH RESOLUTION IMAGE VIEWING

(75) Inventor: Thomas Tahan, La Jolla, CA (US)

(73) Assignee: Opus Medicus, Inc., La Jolla, CA (US)

( * ) Notice: Subject to any disclaimer, the term of this patent is extended or adjusted under 35 U.S.C. 154(b) by 786 days.

This patent is subject to a terminal disclaimer.

(21) Appl. No.: 12/834,810

(22) Filed: Jul. 12, 2010

(65) Prior Publication Data

US 2012/0007866 A1   Jan. 12, 2012

(51) Int. Cl.
*G06F 15/16* (2006.01)
*G06F 15/173* (2006.01)

(52) U.S. Cl.
USPC .......................................... 709/203; 709/224

(58) Field of Classification Search
USPC .................. 345/428, 641, 660, 263, 619; 348/231.99; 382/263; 707/783, 707/E17.031; 725/32
See application file for complete search history.

(56) References Cited

U.S. PATENT DOCUMENTS

| | | | |
|---|---|---|---|
| 6,281,874 B1 * | 8/2001 | Sivan et al. | 707/E17.031 |
| 6,590,583 B2 | 7/2003 | Soohoo | |
| 7,694,234 B2 | 4/2010 | Fleisher et al. | |
| 2002/0194589 A1 * | 12/2002 | Cristofalo et al. | 725/32 |
| 2003/0112347 A1 * | 6/2003 | Wyman | 348/231.99 |
| 2003/0137512 A1 * | 7/2003 | Hoehn et al. | 345/428 |
| 2003/0184561 A1 * | 10/2003 | Vorst | 345/619 |
| 2007/0033542 A1 | 2/2007 | Winser et al. | |
| 2007/0033543 A1 | 2/2007 | Ngari et al. | |
| 2010/0045702 A1 * | 2/2010 | Doyle et al. | 345/641 |
| 2010/0079495 A1 * | 4/2010 | Ubillos et al. | 345/660 |
| 2010/0166334 A1 * | 7/2010 | Zhang et al. | 382/263 |
| 2011/0010776 A1 * | 1/2011 | Ceraolo | 707/783 |

* cited by examiner

*Primary Examiner* — Quang N Nguyen
(74) *Attorney, Agent, or Firm* — Procopio, Cory, Hargreaves & Savitch LLP; Noel C. Gillespie

(57) ABSTRACT

Systems and methods are provided for viewing portions of an image in high resolution and in context with a full image, which is displayed at a base resolution that is lower resolution than the resolution of the high-resolution image. A client device can send a request to a server for a composed image comprised of the base-resolution image overlaid at the area of interest with a virtual lens showing the area of interest in high-resolution image. The request can include the coordinates of the area of interest relative to a reference point on the image, the desired resolution level for the high-resolution image, and the virtual lens size and shape. The desired resolution can fall into a range above the resolution of the base-resolution image and up to the resolution of the maximum-resolution image stored on, generated on, or input to the server.

36 Claims, 12 Drawing Sheets

SYSTEMS AND METHODS FOR NETWORKED, IN-CONTEXT, COMPOSED, HIGH RESOLUTION IMAGE VIEWING

RELATED APPLICATIONS

The present application is related to U.S. patent application Ser. No. 12/834,806, titled "SYSTEMS AND METHODS FOR NETWORKED, IN-CONTEXT, HIGH-RESOLUTION IMAGE VIEWING," filed on Jul. 12, 2010, and issued as U.S. Pat. No. 8,296,359 on Oct. 23, 2012, and U.S. patent application Ser. No. 12/834,809, titled "SYSTEMS AND METHODS FOR COLLABORATIVE, NETWORKED, IN-CONTEXT, HIGH-RESOLUTION IMAGE VIEWING," filed on Jul. 12, 2010, and published as U.S. Patent Publication No. 2012/0011568 on Jan. 12, 2012, both of which are hereby incorporated by reference in their entirety.

TECHNICAL FIELD

The systems and methods described herein generally relates to the field of image processing and more specifically to systems and methods for viewing, over a network, portions of an image in high resolution in the context of the full image.

BACKGROUND

The ability to view high-resolution images downloaded over a network is important for numerous applications. In the medical field, such a capability is of value in the diagnosis and treatment of patients, as well as for research and physician education. Other applications that may benefit from such a capability include engineering, equipment operation and maintenance, digital maps, satellite imagery, forensics, etc. High-resolution images can be extremely large, and can exceed the ability of a computer system to store and display the images. Furthermore, transmission of entire high-resolution images across a network places significant loads on the network and can negatively impact an application's response time if the application has to wait for the image data to be delivered across the network.

SUMMARY

Systems and methods are provided for viewing portions of an image in high resolution and in context with a full image, which is displayed at a base resolution that is lower resolution than the resolution of the high-resolution image. A client device can send a request to a server for a composed image comprised of the base-resolution image overlaid at the area of interest with a virtual lens showing the area of interest in high resolution. The request can include the coordinates of the area of interest relative to a reference point on the image, the desired resolution level for the high-resolution image, and the virtual lens size and shape. The desired resolution can fall into a range above the resolution of the base-resolution image and up to the resolution of the maximum-resolution image stored on, generated on, or input to the server. One or more areas of interest can be specified, each at a specified position, resolution, and virtual lens size and shape.

According to one aspect, a computer-implemented method for displaying a portion of a high-resolution image in the context of a base-resolution image is provided where one or more processors are configured to perform the steps of the method. The method includes the steps of: receiving a request to view an image at a client device, sending a request to a server over a network for a base-resolution image that corresponds to the requested image, receiving the base-resolution image from the server over the network, displaying the base-resolution image on a display of the client device, receiving a request to display an area of interest of the base-resolution image in high resolution, sending a request to the server over the network for a composed image that corresponds to the base-resolution image, receiving the composed image from the server over the network, and displaying the composed image on the display of the client device.

According to another aspect, a computer-implemented method for providing high-resolution imagery is provided where one or more processors are programmed to perform the steps of the method. The method includes the steps of: receiving a request from a client device for a base-resolution image, verifying that the client device or client device's user has access rights to the base-resolution image per an access control policy, generating a base-resolution image based on a maximum-resolution image associated with the requested base-resolution image, transmitting the base-resolution image to the client device via a network connection, receiving a request for a composed image associated with the base-resolution image and area of interest, verifying that the client device or client device's user has access rights to the composed image per the access control policy, generating the composed image, and transmitting the composed image to the client device.

According to another aspect, a technical system for providing high-resolution imagery is provided. The system includes a non-transitory computer readable medium for storing computer executable programmed modules and a processor communicatively coupled with the non-transitory computer readable medium for executing programmed modules stored therein. The system also includes a network interface module stored in the non-transitory computer readable medium and that is configured to receive over a network a request for an image at a selected resolution from a client device, transmit the image to the client device over the network if the client device or a user of the client device has access rights to the image; receive over a network from a client device a request for a composed image comprised of a portion of a high-resolution image corresponding to an area of interest overlaid over a base-resolution image at a location corresponding to the area of interest, and transmit the composed image to the client device over the network if the client device or a user of the client device has access rights to the image. The system also includes a request processing module stored in the non-transitory computer readable medium and that is in communication with the network interface module. The request processing module being configured to receive the request for an image at the selected resolution from the network interface module, process the request for the image at the selected resolution, send the requested image at the requested resolution to the network interface module for transmission to the client device; receive the request for the composed image from the network interface module, process the request for the composed image, and send the composed image to the network interface module for transmission to the client device. The system also includes an access control module stored in the non-transitory computer readable medium and in communication with the request processing module. The access control module is configured to receive an authorization request from the request processing module to verify access rights of the client device or a user of the client device to the requested image, verify the access rights per an access control policy, and send an authorization response to the request processing module indicating whether the client device or the user has access rights to the image. The system also includes an image management module stored in the non-transitory computer readable medium in communication with the request processing module. The image management module being configured to process an image management request using a data store.

According to another aspect, a technical system for viewing high-resolution imagery is provided. The system includes a non-transitory computer readable medium for storing computer executable programmed modules and a processor communicatively coupled with the non-transitory computer readable medium for executing programmed modules stored therein. The system also includes a network interface module stored in the non-transitory computer readable medium and that is configured to transmit a request for an image to a server over a network, receive the requested image from the server over the network, transmit a request for a composed image to the server over the network, and receive the composed image from the server over the network. The system also includes a user interface module stored in the non-transitory computer readable medium and configured to receive a request from a user to view an image, receive a base-resolution image corresponding to the requested image, display the base-resolution image on a display of the system, receive a request from the user to display an area of interest of the base-resolution image in high resolution, send a request to the request processing module for a composed image comprised of a portion of a high-resolution image corresponding to the area of interest overlaid on the base-resolution image at a location that corresponds to the area of interest, receive the composed image from the request processing module, and display the composed image on a display of the system. The system also includes a request processing module stored in the non-transitory computer readable medium and in communication with the user interface module and the network interface module. The request processing module is configured to process a request for a base-resolution image from the user interface module, and process a request for a composed image from the user interface module. The system also includes an image management module stored in the non-transitory computer readable medium and in communication with the request processing module and network interface module. The image management module being configured to process an image management request using a data store.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

Figure 1:
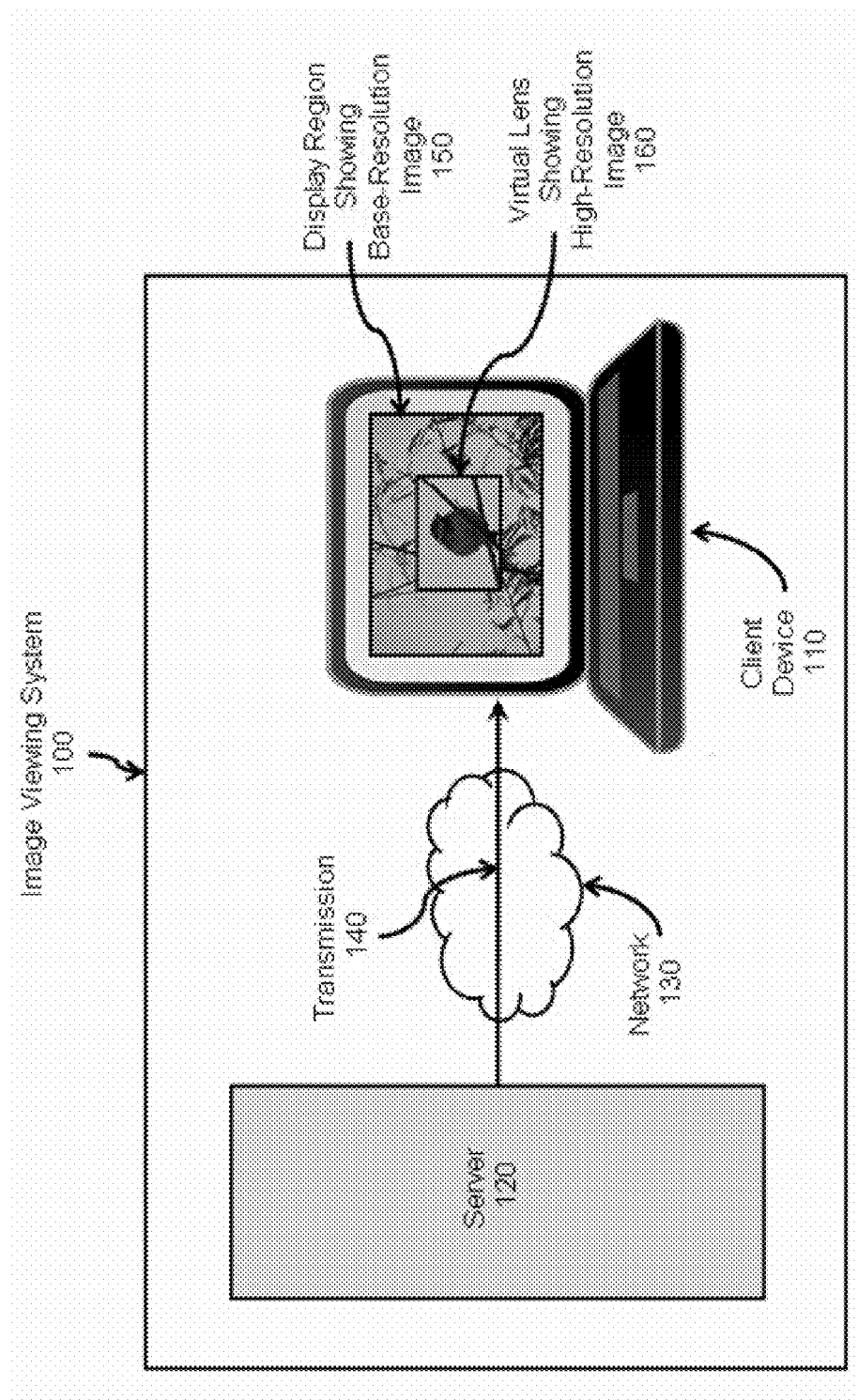
FIG. 1 is a block diagram illustrating an image viewing system according to an embodiment.

Systems and methods are provided that facilitate the viewing of high-resolution portions of an image on a client device using a virtual lens. In response to a user request to view an image, the client device can request a copy of the image at a base level resolution from a server over a network. The server can generate, retrieve from storage, or input the base-resolution image from a high quality, high-resolution image that is stored on, generated on, or input to the server and transmit the base-resolution image to the client device. The base-resolution image is of a lower resolution than the high-resolution image that is stored on, generated on, or input to the server, and the resolution of the base-resolution image can be determined at least in part based on the capabilities of the client device or network. The client device is configured to receive the base-resolution image from the server and to display the base-resolution image on a display interface. A user of the client device can then select an area of interest on the base-resolution image, and the client device can request a high-resolution image from the server that corresponds to the area of interest identified by the user, the high-resolution image being of a resolution up to the resolution of the image stored on, generated on, or input to the server. For example, in some embodiments, the client device can be configured to render a "virtual lens" that is overlaid on the base-resolution image at the area of interest, and to display within the virtual lens the portion of the high-resolution image that corresponds to the area of interest. The virtual lens can thus show a more detailed image of the area of interest, enabling the user to "zoom in" on details within an area of interest. The size of the virtual lens and the resolution of the high-resolution image displayed within it can be determined at least in part based on the capabilities of the client device or network.

In some embodiments, only a portion of the high-resolution image that corresponds to the area of interest or a region of the image that includes the area of interest can be sent to the client device by the server. In other embodiments, a full high-resolution image can be sent to the client device by the server and the client device can be configured to select a portion of the high-resolution image that corresponds to the area of interest and to display that portion of the high-resolution image in the virtual lens.

According to an embodiment, an overlay image provided by the virtual lens can be located on a portion of the full, base-resolution image that corresponds to the higher-resolution image displayed by the virtual lens in order to provide context as to the location of the high resolution portion with respect to the image, as well as select the level of resolution. This configuration enables viewing of high-resolution images within the available display space of an application while providing context to the overlaid image. According to an embodiment, these techniques can be used to display high resolution content corresponding to at least a portion of an image, even where the resolution of a computer system is insufficient to show the full image at high resolution or where it is undesirable to use an amount of display space that would be necessary to show an entire high-resolution image.

Some embodiments enable a user to select an area of interest within the image to be displayed in high resolution, and some embodiments provide the user with the ability to move the area of interest to any part of an image. These techniques can help to reduce the amount of high-resolution image data that needs to be sent across the network at a given time, and can also reduce the amount of display area required on the device displaying the image data as well as processing power, memory, or both of the client device and server. Furthermore, embodiments can be used to optimize the response times for various usage scenarios.

FIG. 1 is a block diagram of an image viewing system 100 according to an embodiment. The image viewing system includes a client device 110, a server 120, and network 130. Client device 110 can be a computing device comprising one or more processors, volatile and non-volatile memory, displays, keyboards (hard or soft), pointing devices (e.g., mouse, touch pad, joystick, touch screen, track ball), network interfaces, and other input/output devices. The client device 110 can be a desktop computer, laptop computer, a computer workstation, computing pad, computing tablet, document reader, smart phone, cell phone, personal digital assistant, network appliance, thin client system, digital television with embedded or external processor, memory, and network interface, or other type of device capable of receiving image data over a network and displaying the image data to a user of the device. According to some embodiments, the functionality of client device 110 can be implemented in one piece of equipment or be distributed across multiple pieces of equipment.

Server 120 can be a computing device comprising one or more processors, volatile and non-volatile memory, network interfaces, and other input/output devices. According to some embodiments, the functionality of server 120 can be implemented in one piece of equipment or be distributed across multiple pieces of equipment. According to some embodiments, the image viewing system 100 can include multiple servers 120 that are configured to provide image data to one or more client devices 110 via one or more networks 130. The server 120 can, in some embodiments, be a web server that is configured to provide content to the client device 110 over the network 130. According to an embodiment, the server 120 can be in communication with one or more data stores (not shown) that can be used to store image data to be provided to the client device. According to an embodiment, the data stores can be implemented on the server 120 or can be implemented on a separate data server (not shown). The server can also be in communication with one or more image input devices (e.g., a camera, a scanner, a sensor).

According to an embodiment, the network 130 can represent one or more wired or wireless network connections between server 120 and client device 110. According to an embodiment, network 130 includes the Internet, a local area network, a wide area network, a metropolitan area network, a telephone network, a television network, a wireless network or link, a satellite network or link, a bus, or other type of network or interconnection method.

According to an alternative embodiment, the functionality of the server 120 and client device 110 can be implemented in a single device or piece of equipment. For example, the techniques disclosed herein can be used for viewing data captured by a digital microscope scanning system.

The image viewing system 100 enables a user to view portions of a high-resolution image on the client device 110 without requiring that the entire high-resolution image be transmitted by the server 120 to the client device 110. In an embodiment, the client device 110 can be configured to display a "base-resolution" image in a display region 150 of the client device 110 and a virtual lens 160 overlaid on the base-resolution image in display region 150. The base-resolution image can be a lower resolution representation of a high-resolution image stored on, generated on, or input to the server 120. Because the base-resolution image is a lower resolution than the high-resolution image, the base resolution image requires less bandwidth to be transmitted over the network 130 to the client device 110. The base-resolution image in display region 150 can provide a user of client device 110 with a context in which the user can identify areas of interest to be displayed in high-resolution.

The virtual lens 160 can display a high resolution portion of the base-resolution image in display region 150 at a higher resolution than the base-resolution image. According to an embodiment, the resolution of the portion of the high-resolution image displayed in virtual lens 160 can be the same as the resolution of the high-resolution image stored on, generated on, or input to the server 120. According to another embodiment, the resolution of the portion of the image displayed in the virtual lens 160 can be of a different resolution than the high-resolution image stored on, generated on, or input to the server 120. For example, the virtual lens 160 can be configured to display a portion of the high-resolution image at a resolution that is between that of the base-resolution image 160 and the resolution of the high-resolution image stored on, generated on, or input to the server 120. According to an embodiment, the user can select the resolution at which the virtual lens 160 displays the image from a discrete set of resolutions. The image viewing system 100 can determine the resolution levels of the discrete set of resolution based in-part on the capabilities of the client device or network, and the resolution of the base-resolution image. In another embodiment, the user can select the resolution at which virtual lens 160 displays the image from a continuous range of resolutions. The image viewing system 100 can determine the lower and upper bounds of the continuous range of resolutions based in-part upon the capabilities of the client device or network, and the resolution of the base-resolution image.

According to an embodiment, the high-resolution images can be uploaded to server 120, generated on server 120, or be generated by equipment coupled to the server 120, such as a digital scanning microscope, a digital camera, or a scanner.

According to an embodiment, a user of client device 110 can select an area of interest of the base-resolution image in display region 150 that corresponds to a portion of the high-resolution image that the user would like to view in the virtual lens 160. According to an embodiment, the client device can be configured such that a user can select a portion of the base-resolution image in display region 150 using a pointing device of the client device 110, such as a mouse, trackball, touchpad, touch screen, joystick, arrow keys, buttons, or other input device. According to an embodiment, the client device can be configured such that a user can also select a different area of interest using a pointing device of the client device 110 by selecting an area on the base-resolution image in display region 150. According to an embodiment, the client device 110 is configured to display in display region 150 the full lower-resolution base image overlaid with a portion of the high-resolution image corresponding to the area of interest selected on the base-resolution image. Because the portion of the high-resolution image displayed in the virtual lens is of higher resolution than the base-resolution image, less of the image can be shown in the virtual lens than the area that it covers in the base-resolution image. The capability to cause the virtual lens to move using the pointing device enables the user of the client device to eventually see all parts of the image in the virtual lens at high resolution.

The term "resolution," as used herein, refers to the total number of pixels of an image and can also refer to the total number of colors per pixel for an image. For example, resolution can refer to the total number of horizontal pixels by the total number of vertical pixels in an image. In yet other embodiments, an optional third dimension can be included, and the resolution can include a depth component. The resolution may also include a time dimension if the image changes in time. With respect to video content, resolution can refer to the total number of frames per second. The resolution can alternatively refer to the level/quantity of details of an image. For example, the number of roadways or other features illustrated on a map.

In certain embodiment, three levels of resolution can be used here to distinguish between different resolutions for an image:

Maximum resolution is a resolution that is less than or equal to the resolution at which an image is captured (e.g., via a digital camera, scanner, or sensor), input, or generated (e.g., with image or video authoring tools).

Base resolution is a resolution that is sufficient for basic inspection of an image, as well as sufficient to provide a visual context for viewing a portion of a high-resolution image. The base resolution is a lower resolution than the maximum resolution.

High resolution is a resolution that is higher than the base resolution and less than or equal to the maximum resolution.

Top resolution is a resolution that is greater than or equal to high resolution and less than or equal to the maximum resolution.

In one example, a high resolution still image can be 3648× 2736 pixels (horizontal by vertical) with 24-bits of color per pixel, typical of digital cameras with 10 megapixel resolution. However, one skilled in the art will recognize that this is merely one example and that the resolution of the high-resolution images can vary.

A typical high-resolution image can consume a significant amount of memory, and can be too large to fully view at the native resolution in the available area of a client's display. A typical high-resolution image can also take a considerable amount of time (e.g., several seconds or more) to download from the server over the network, or can otherwise stress the capabilities of the client, server, or network. In many applications, a base (low-to-medium) resolution image can be sufficient for basic inspection of the image. A user occasionally needs to see areas of interest of the image at high resolution (higher resolution than the base resolution) to inspect details of the image. In certain embodiments, the user is allowed to view a high-resolution portion of an image shown in the context of the base-resolution image.

Some conventional image viewing systems allow a user to magnify a portion of an image, but these systems typically magnify a portion of the computer display using digital magnification methods rather than obtaining and displaying a higher resolution image that can actually contain additional detail. In some conventional systems, a portion of a bitmap corresponding to an image being displayed to user is digitally enlarged to create a magnification effect. This approach does not provide any additional detail, but rather uses digital enhancement of a lower resolution image to create the simulated magnified image. For example, the pixels in the original lower resolution image can be replicated to create the simulated magnified image, and one or more smoothing algorithms might be applied to the magnified image. However, the resulting simulated magnified image can be grainy and can lack additional detail that was not in the original image. Some conventional systems also magnify the whole image rather than just a user-selected area of interest within the image. For example, ADOBE READER® and MICROSOFT OFFICE® magnify a whole image or document page rather than a user-selected area of interest within an image or document page.

In contrast, the image viewing system 100 can display in high resolution user-selected areas of interest of an image that has been captured or generated at a maximum resolution. The client device 110 can display the user-selected area of interest with up to all of the detail available at the maximum resolution and can show the area of interest in context of the full image at the base-resolution. According to an embodiment, a user-selected area within the image is displayed in high resolution overlaid on the full base-resolution image at the area of interest selected by the user.

Conventional systems also do not use a client-server based approach to digital magnification or in-context high-resolution display. In conventional systems, images or documents are stored locally on a computer system and all or a portion of the document can be magnified using the conventional techniques described above. In contrast, the image viewing system 100 can use a client-server based approach where the large high-resolution images are stored on, generated on, or input to the server 120 and a smaller base-resolution image can be transmitted across the network 130 to the client device 110 for basic inspection. The high resolution image can be transmitted only as needed and not necessarily for every base-resolution image, thereby saving network bandwidth as well as processing and memory resources on both the client device and the server. In some embodiment, as a further optimization, if the user is expected to require viewing of only a portion of the image in high resolution, that portion can be transmitted by the server to the client device across the network 130, rather than the entire high-resolution image. Since a high-resolution image can be in the order of a megabyte or more in size even when compressed, reducing the number of times that it is transmitted or merely sending across the network the portions of a high-resolution image corresponding to the areas of interest that the client device user selects can provide an efficient system for viewing images that can provide a good overall response time.

Returning now to FIG. 1, client device 110 of the image viewing system 100 can be configured to allow a user to view images stored on, generated on, or input to the server 120 at various resolutions. The display region 150 on the client device 110 shows a base-resolution image and the virtual lens 160 shows a high-resolution portion of the image that is overlaid over the base-resolution image. According to an embodiment, the display region 150 can be all or part of a display window of an application running on the client device 110, such as web browser, a word processing application, an image viewer or editor application, or other type of application in which a user might wish to view high-resolution image content.

According to an embodiment, the client device 110 can be configured to display the virtual lens 160 using different shapes. For example, the virtual lens can be rectangular, circular, ovular, or another shape. According to some embodiments, the virtual lens can include accessories, such as a frame and handle. For example, in one embodiment, the virtual lens can be shaped like a magnifying glass in order to provide the illusion of a moveable magnifying glass that overlays the base-resolution image and within the magnifying glass shaped virtual lens 160, a portion of the high-resolution image associated with the area of interest selected by the user is displayed. The high-resolution image can be transmitted (transmission 140) from the server 120 to the client device 110 via network 130.

According to an embodiment, the client device 110 can be configured to allow the user to move, using a pointing device, the virtual lens 160 over the base-resolution image in display region 150 in order to change the portion of the high-resolution image displayed in the virtual lens 160. As described above, while the virtual lens 160 appears to operate as a magnifying glass on the base-resolution image in display region 150, no actual magnification of the base-resolution image is performed. Instead, the virtual lens 160 displays the portion of the high-resolution image received from the server 120.

For example, an online medical continuing education course provider can use the image viewing system 100 to display training slides that include digital microscope imagery. These digital images can be extremely large in size and can consume a lot of network bandwidth if an entire high-resolution image is transmitted from the server 120 to the client device 110. Instead of providing a full sized high-resolution image, the server 120 can provide base-resolution image of a digital slide that illustrates a particular concept. If the user would like to see more detail, the user can select an area of interest on the base-resolution image and the client device 110 can present a high-resolution view of the area of interest in the virtual lens 160 overlaid over the area of interest of the base-resolution image. The user can see a higher level of detail in the high-resolution image for that image. This approach can make more efficient use of network and computing resources of the server 120 and the client device 110, because the client device does not need to request the high-resolution image from the server 120 for every base-resolution image viewed. Further efficiencies can be achieved when the user only needs to view a portion of the image in high resolution (e.g., a region surrounding a selected area of interest), since only that portion may be transmitted from the server to the client device, rather than the entire high-resolution image. In some embodiments, the location of the virtual lens 160 can be configured to appear at a particular location on the base-resolution image in order to highlight a particular feature from the digital slide that illustrates a point from the teaching materials. In some embodiments, the user can also dynamically control the positioning and the size of the virtual lens 160, and the contents of the virtual lens 160 can be dynamically updated with high-resolution content from the server 120 as the user changes the area of interest. In some embodiments, the user can also change the level of "magnification" (i.e., the level of resolution) displayed by the virtual lens. If the user requests that the virtual lens zoom in further, a higher resolution image can be displayed in the virtual lens (up to a maximum resolution supported by the server), and if the user requests that the virtual lens zoom out, a lower resolution image can be displayed in the virtual lens.

In another example, an online mapping application can use the image viewing system 100 to display additional details about an area of interest, to display more detailed satellite imagery of an area of interest, or both. When the user requests a map, the server 120 can provide a base-resolution map to the client device, and the virtual lens can be used to provide a detailed view of a portion of the map in the context of the base-resolution image, when the user requires a more detailed view. Thus, the high-resolution image can be downloaded only when needed. In some embodiments, as a further optimization, when the user's high-resolution viewing requirement is only for a portion of the image (e.g., a region surrounding a selected area of interest), only that portion may be transmitted from the server the client device over the network. This technique could be particularly useful on mobile devices that include navigation applications, because these devices often have bandwidth and memory constraints.

According to an embodiment, the image viewing system 100 can be configured to use three different modes of operation: a successive download method, a client downscaling method, and a server composition method. According to some embodiments, these methods can be used alone or in combination. In another embodiment, the image viewing system 100 can be configured to provide a collaborative method that can be used in combination with either the successive download method, the client downscaling method, or the server composition method.

Successive Download Method

Figure 2:
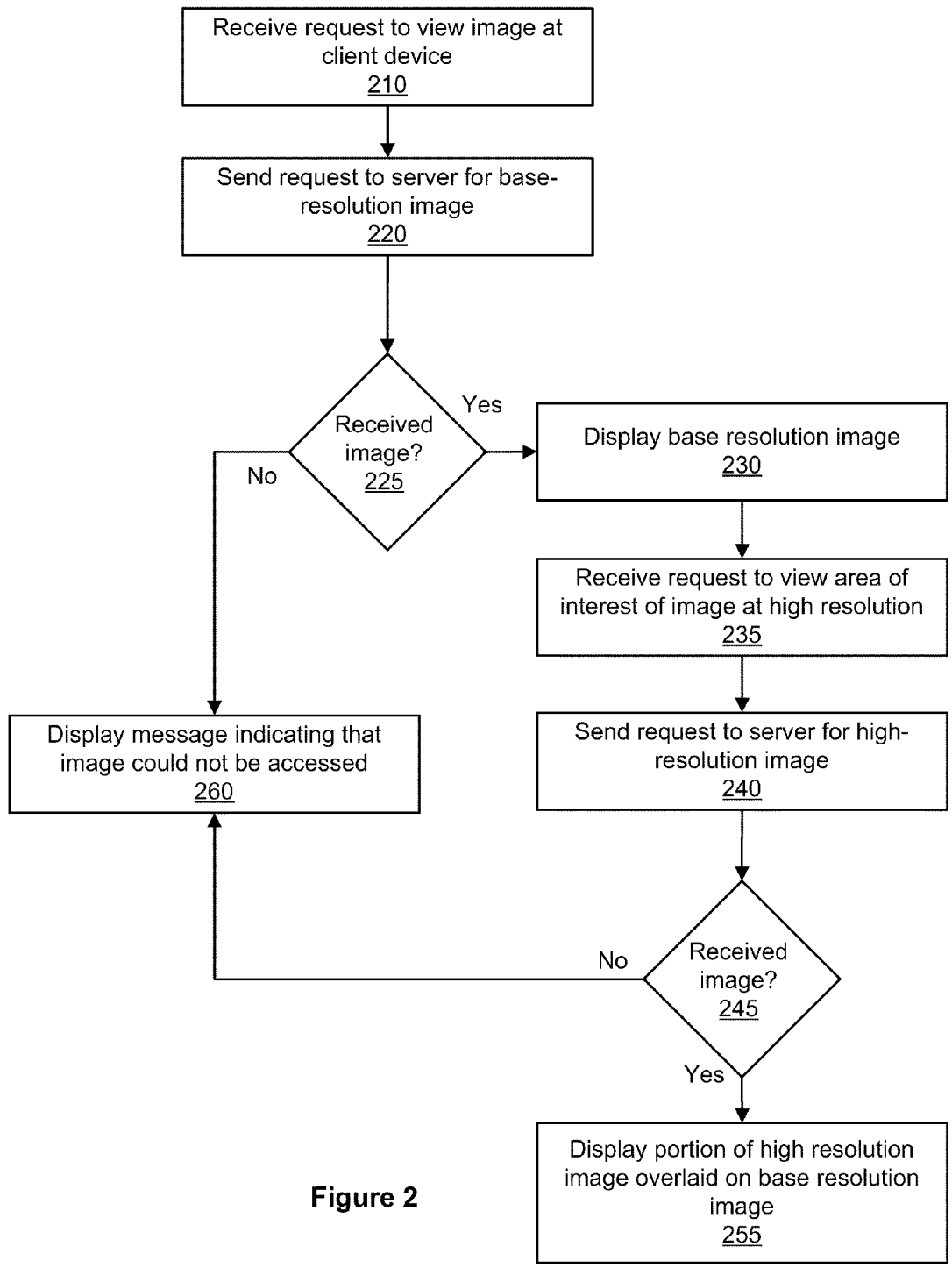
FIG. 2 is a flow diagram of a successive download method that can be implemented on a client device of the image viewing system illustrated in FIG. 1 according to an embodiment.
Figure 3:
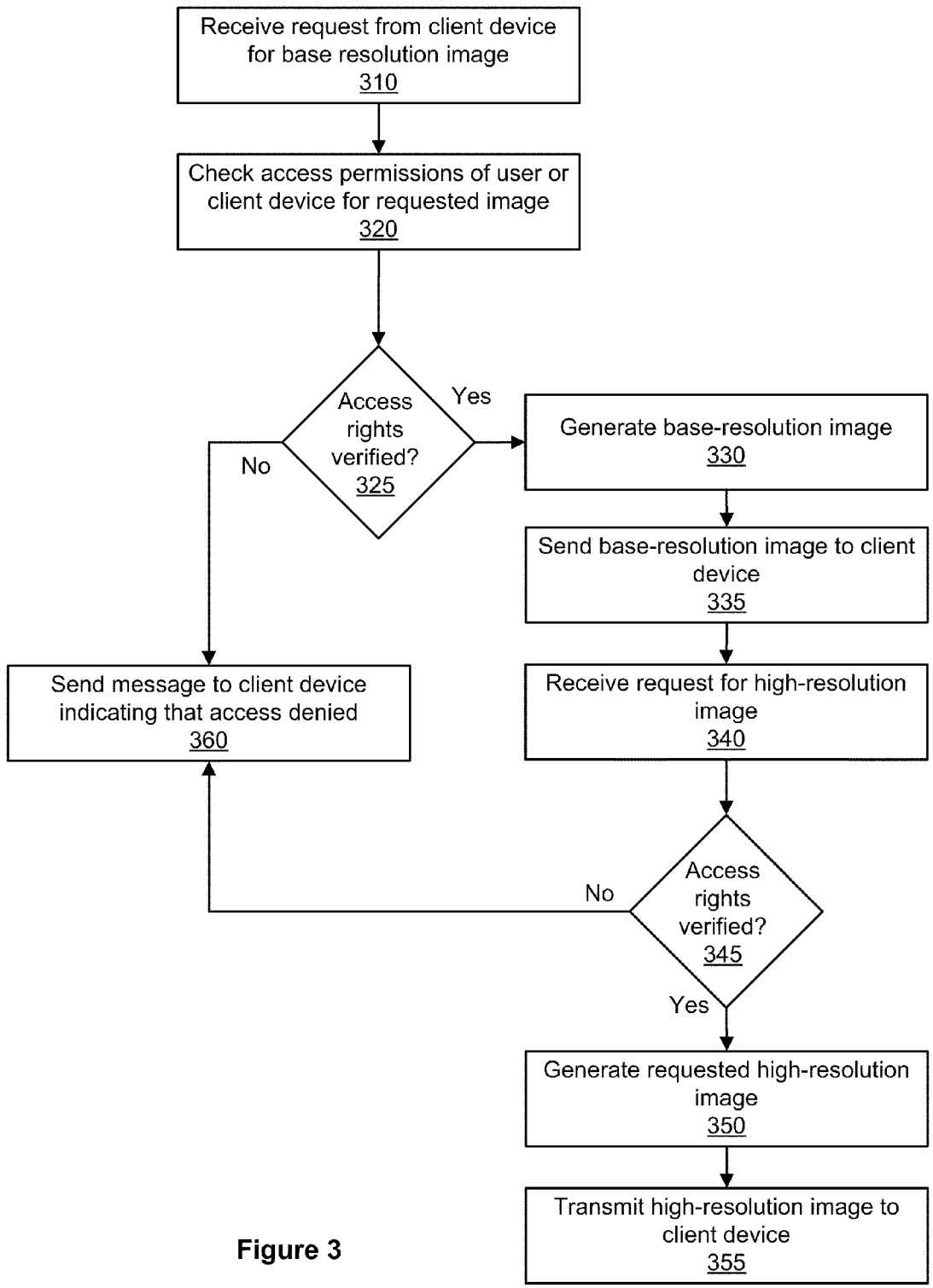
FIG. 3 is a flow diagram of a successive download method that can be implemented on a server of the image viewing system illustrated in FIG. 1 according to an embodiment.

FIGS. 2 and 3 are flow diagrams of a successive download method that can be used in conjunction with an image viewing system 100 according to an embodiment. FIG. 2 illustrates the steps of a method for successive download that can be performed at client device 110 according to one embodiment, and FIG. 3 illustrates the steps of a method for successive download that can be performed by server 120.

The method of FIG. 2 begins when a client device 110 receives a request to view an image at the client device (step 210). According to an embodiment, the request can comprise a user accessing a document or image from an application. In other embodiments, the request can comprise a user accessing a particular web page or other content from a browser application running on the client device 110. In yet another embodiment, the request can comprise a user executing an application on the client device 110 that uses high-resolution image content retrieved from the server 120.

In the example of FIG. 2, the client device 110 sends a request to the server 120 for a base-resolution image (step 220) that corresponds to the image that was requested. According to an embodiment, a display engine module can be implemented on the client device 110 that is configured to process requests for images from applications on the client device 110 and to send a request via network 130 to the server 120 for a base-resolution image that corresponds to the requested image.

A determination is made whether the image was received from the server 120 (step 225). According to an embodiment, if access to the image is to be restricted, the server 120 can make a determination whether the user of the client device or the client device 110 (or both) is authorized to view the image content requested per the access control policy. According to an embodiment, the request sent by the client device 110 can include identification information associated with a user or the client device 110 that can be used in determining whether the server 120 should grant access to the image content stored on, generated on, or input to the server 120. If the user is not authorized to access the requested image, the server 120 can optionally send a message to the client device 110 indicating that the user or client device 110 is not authorized to access the requested image. According to an embodiment, the client device 110 can also be configured to keep track of how much time has passed since the request was transmitted to the server 120 and to timeout the request if the base-resolution image is not received within a predetermined amount of time.

If the image is not received from the server 120, the client device 110 can optionally display a message to the user indicating that the requested image could not be accessed (step 260). According to some embodiments, a detailed error message can be generated that describes why the image could not be accessed. For example, the message can indicate that the request timed out if a response was not received within a predetermined amount of time, or that the user was not authorized to view the requested content.

Figure 4:
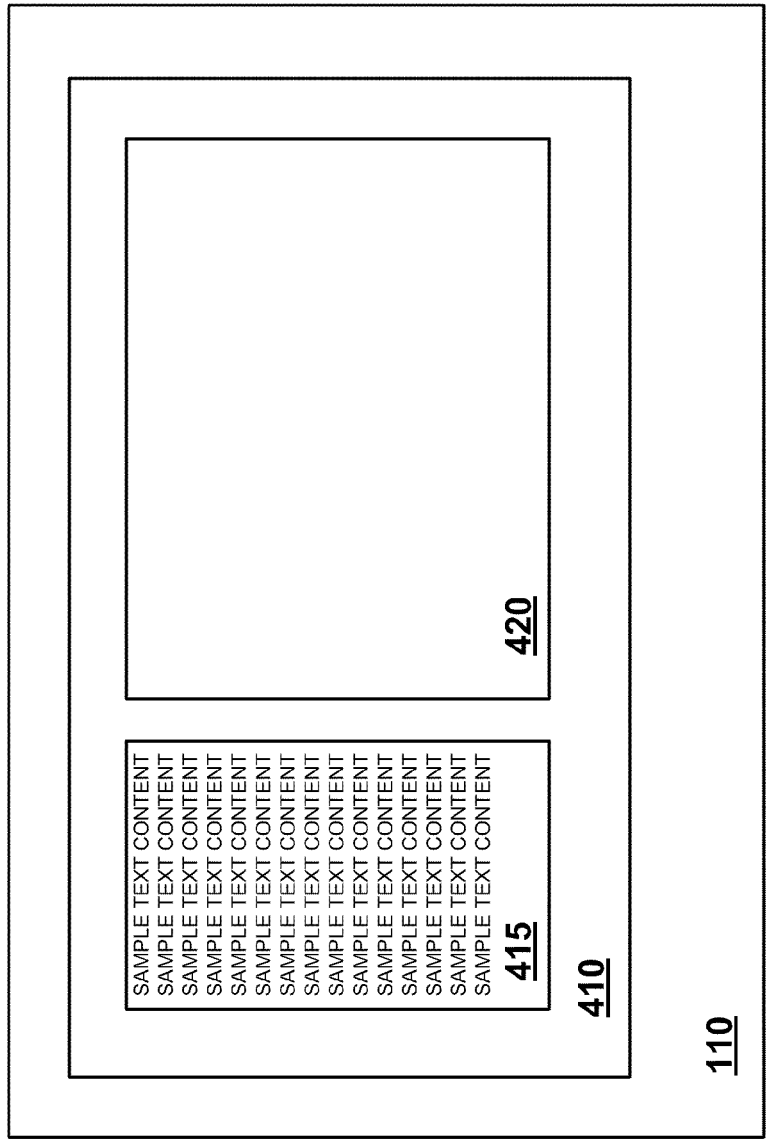
FIG. 4 is a block diagram of an example display area of a client device according to an embodiment.

If the image is received by the client device 110 from the server 120, the client device 110 can display the base-resolution image in display region 150 of the client device 110 (step 230). According to an embodiment, the display engine of the client device can be configured to adjust the size of the base-resolution image based on the available space on the display area of the client device 110 for displaying the base-resolution image. FIG. 4 illustrates an example of a display area on a client device. For example, if the client device 110 includes a 1200 pixel wide by 800 pixels high display area 410, and if 60% of the width of display area is available for displaying the base-resolution image 420, and the full height minus 140 pixels at the top of the display area and minus 120 pixels at the bottom of the display area is available, the display engine module of the client device will display the base-resolution image as a 720 pixel wide by 540 pixel high image on the display area on the available display area 420. According to an embodiment, the display area 410 can comprise a desktop displayed on a screen or other display device of client device 110. In an embodiment, the display area 410 can comprise a window of an application, including the application information as well as window controls and other information. For example, in some embodiments, a user can access content, such as high-resolution imagery or a web page or other content that includes high-resolution imagery from within a browser. In the embodiment illustrated in FIG. 4, a portion of the display area 415 is being used for text content, which reduces the available space for displaying the base-resolution image. The available space for displaying the base-resolution image can also be affected if the base-resolution image is to be displayed in an application window. As a result, the display area 420 for the base-resolution image can be less than the total amount of display area for the client device's display. As can be seen from these example embodiments, the resolution of the base-resolution image can be based at least in part by the resolution and screen size of the client device 110 and can also be based on the size of the display area 420 available for showing the base-resolution image.

The client device 110 can then receive a request from the user to view an area of interest of the image in high resolution (step 235). According to an embodiment, the user can use an input device, such as a pointing device, including a mouse, touch screen, touchpad, joystick, trackball, arrow keys, buttons, or other input device that allows the user to select an area of interest within the base-resolution image that the user would like to view in high resolution.

The client device can then send a request to the server 120 for a high-resolution image that corresponds to the base-resolution image (step 240). According to an embodiment, the request can include a desired resolution level for the high-resolution image. The desired resolution can fall into a range above the resolution of the base-resolution image and up to the resolution of the maximum-resolution image stored on, generated on, or input to the server 120.

According to some embodiments, the client device 110 can send a request to the server 120 for only the portion of the high-resolution image that contains the area of interest identified by the user, rather than the full high-resolution image. The alternative of requesting only a portion of the high-resolution image may be used, for example, if the user is expected to only view part of the base image in high resolution, of if the network transmission time for the full image would adversely affect response time, or if client memory size is inadequate for the full high-resolution image. According to an embodiment, the request can include a set of coordinates relative to a reference point on the base-resolution image that correspond to the area of interest. For example, in some embodiments, the client device 110 is configured so that a user can draw a rectangle on the base-resolution image to indicate the area of interest that the user would like to see in high resolution, and coordinates of the left-top and right-bottom corners of the rectangle, or the coordinates of the left-top or center point and the width and height of the rectangle, can be provided to the server 120 in the request for the high-resolution image. According to an embodiment, the display engine module can be configured to translate screen coordinates to pixel coordinates on the base-resolution image, and the request to the server for the high-resolution image can include the pixel coordinates of the area of interest specified by the user. According to an alternative embodiment, the client device 110 can provide a user interface where the user can drag or move a cursor or a shape, such as a rectangle or oval, to the location of an area of interest on the base-resolution image in order to receive a high-resolution image that corresponds to the area indicated by the cursor or covered by the shape.

A determination is made whether the high-resolution image was received from the server 120 (step 245). If the image is not received from the server 120, the client device 110 can optionally display a message to the user indicating that the requested image could not be accessed. Otherwise, if the requested high-resolution image corresponding to the area of interest is received by the client device 110, the client device 110 can display the portion of the high-resolution image corresponding to the area of interest in the virtual lens 160 (step 255). The virtual lens can be positioned over the area of interest on the base-resolution image and can be configured to display the portion of the high-resolution image that corresponds to the area of interest identified by the user. According to an embodiment, the virtual lens 160 can default to an initial size and shape. In one embodiment, the size of the virtual lens can correspond to the size of the base-resolution image displayed on the client device 110. For example, in one embodiment, the size of the virtual lens might be one fourth of the size of the base-resolution image. For example, if the size of the base-resolution image is 720 pixels wide by 540 pixels high, the size of the virtual lens would be 360 pixels wide by 270 pixels high.

According to an embodiment, the display engine module of the client device 110 can determine the portion of the high-resolution image corresponding to the user-selected area of interest and display the corresponding portion of the high-resolution image in the virtual lens 160, replacing the underlying base-resolution image in the area of interest with the corresponding portion of the high-resolution image. According to one embodiment, if the user selected horizontal and vertical coordinates [180,270] relative to the left-top on the base-resolution image as the center of an area to be shown in higher resolution, the virtual lens can be positioned centered at [180,270] on the base-resolution image. If the resolution of the high-resolution image is 1080 pixels wide by 810 pixels high and the portion of the high-resolution image to be displayed (e.g., the size of the virtual lens) is 360 pixels wide by 270 pixels high, the center point of the area to be displayed in the high-resolution image would be [270,405], the point corresponding to [180,270] in the base-resolution image (a quarter of the way across and halfway down). According to some embodiments, a border can also be rendered around the virtual lens 160 to demarcate the virtual lens 160 from the base-resolution image in display region 150. It should be noted that a smaller area of the high-resolution image can be displayed in the virtual lens than the area in the base-resolution image that the virtual lens covers. In this example, in a 360×270 virtual lens, approximately 11% of the high-resolution image can be shown in the virtual lens ((360×270)/(1080×810)). The virtual lens would cover approximately 25% of the base-resolution image ((360×270)/(720×540), not including borders). The ability to move the virtual lens over the high-resolution image enables all parts of the base-resolution image to be viewed in high resolution in the virtual lens.

According to an alternative embodiment, in order to improve response time, the high-resolution image can be downloaded from the server 120 in advance of a user's request to view the portion of the high-resolution image in the virtual lens 160. In such an embodiment, the portion of the high-resolution image is not displayed in the virtual lens 160 until such display is requested by the user. According to an embodiment, the pre-fetch of the high-resolution image can be initiated by some user action, which can trigger the client device 110 to send a request the server 120 for the high-resolution image. For example, in some embodiments, the download of the high-resolution image can be requested at the time the base-resolution image is requested from the server 120, or shortly after the base-resolution image is received from the server. Alternatively, the client device 110 can be configured to initiate the download of the high-resolution image in response to the user depressing a soft or hard key (e.g., an "image viewing system activate" button) or by clicking on a pointing device button. Continuing this pre-loading technique, a subsequent download of the image at the next higher resolution can be requested upon completion of each high-resolution image download, up to the maximum resolution.

According to an embodiment, the client device 110 can be configured to allow the user to move the virtual lens 160 over the base-resolution image in display region 150. In one embodiment, the client device 110 is configured such that the user can move the virtual lens using a pointing device, such as mouse, touchpad, touch screen, joystick, trackball, arrow keys, or buttons. In an embodiment, the display engine module of the client device 110 is configured to change in real time, as the user moves the cursor across the base-resolution image, the selected area of interest and the position of the virtual lens overlaid on it, while changing the portion of the high-resolution image displayed in the virtual lens to correspond to the changed area of interest indicated by the cursor position. According to an embodiment, the display engine takes into account the cursor position within the base-resolution image relative to a point of reference, such as the left-top corner of the image to determine the position of the high-resolution image to display within the virtual lens 160. In an embodiment, the display engine module can also take into account whether the user has scrolled the display on the client device display and adjust for horizontal or vertical scrolling amounts (or both). If a portion of the high-resolution image had been requested from the server 120 rather than the full high-resolution image, if the cursor moves to a location such that more of the high-resolution image is needed to fill the virtual lens 160, the client device 110 can send a request to the server 120 for an additional portion of the high-resolution image to display in the virtual lens 160.

According to an embodiment, the display engine module of the client device 110 can be configured to allow a user to request a change in the level of resolution of the high-resolution image displayed in the virtual lens 160. According to an embodiment, the display engine module can be configured to provide user interface controls, such as soft buttons, sliders, pointer device controls, or other types of interface components with which the user can interact to select a desired level of resolution for the high-resolution image displayed in the virtual lens 160. In an embodiment, the user can select a level of resolution for the image displayed in the virtual lens 160 that is up to the maximum resolution level of the image stored on, generated on, or input to the server 120. In an embodiment, the user can select a level of resolution that is up to the maximum resolution and greater than the resolution of the base-resolution image.

In response to a request to change the resolution of the portion of the image displayed by the virtual lens 160, the display engine module can be configured to send a request to the server 120 for the full high-resolution image or a portion of the high-resolution image corresponding to the base-resolution image and the selected resolution level. When a portion is requested, the portion requested may be the same size as what will be displayed in the virtual lens 160 or larger. The display engine module can display the portion of the high-resolution image corresponding to the area of interest in the virtual lens 160 once the server 120 sends the high-resolution image to the client device 110 over the network 130. When the user requests an increase in resolution over what is currently being displayed in the virtual lens 160, a portion of the high-resolution image of the requested resolution that corresponds to a smaller portion than currently shown of the base-resolution image will be displayed in the virtual lens 160. When the user requests a decrease in the resolution relative to what is currently being displayed in the virtual lens 160, a portion of high-resolution image that corresponds to a larger portion than currently shown of the base-resolution image will be displayed in the virtual lens 160. According to an embodiment, the server 120 can have a plurality of images of different resolutions for a particular base-resolution image stored in memory, each image in the plurality of images generated from an image of greater than or equal resolution generated on, input to or stored on server 120, or the server 120 can store the maximum-resolution image in memory and generate other high-resolution images (of lower resolution than the maximum) upon request from the client. According to an embodiment, a user can change the resolution displayed by the virtual lens 160 on the fly.

According to an embodiment, the display engine of the client device 110 can also be configured to allow a user to change the size of the virtual lens 160 as well as the resolution of the image displayed by the virtual lens 160. According to an embodiment, the display engine can provide controls that comprise soft buttons (buttons or other interface components drawn on the client device display and selected with the pointing device), hard buttons (keyboard or other buttons or switches), or pointer device controls (e.g., left or right mouse button clicks, mouse button down or up, track wheel controls, track ball controls, touch-sensitive controls, or other pointer device controls). According to an embodiment, the display engine can also be configured to provide controls that enable a user to freeze the virtual lens at its current position (i.e., stop it from tracking the pointing device movement), or unfreeze the virtual lens (resume tracking the pointing device movement). According to an embodiment, the display engine can also be configured to provide controls that enable a user to turn off the virtual lens display, such that the full base-resolution image is shown without the high resolution overlay, or to turn the virtual lens display back on. Some controls can perform multiple functions, such as changing both the virtual lens size and resolution of the image displayed by the virtual lens 160 together.

The method illustrated in FIG. 3 illustrates the steps taken by the server 120 that correspond to the steps performed by the client device 110 in FIG. 2. The server 120 receives a request for a base-resolution image from the client device 110 (step 310). If access is to be restricted, the server 120 can check whether the user or client device 110 has access rights to the requested image (step 320) per an access control policy. According to an embodiment, when access to the image is to be restricted, the request sent by the client device 110 can include identification information associated with a user or the client device 110 that can be used in determining whether the server 120 should grant access to the image content stored on, generated on, or input to the server 120.

A determination is made whether the user or client device 110 (or both) has access rights for the requested image (step 325). If the user or client device 110 does not have access to the requested image, the server 120 can be configured to send a message to the client device 110 indicating that the user or client device 110 does not have access to the requested content (step 360). Otherwise, if the user has access to the requested image, the server 120 can generate a base-resolution image (step 330) from a high-resolution image of greater than or equal resolution stored on, generated on, or input to the server 120 and associated with the base resolution image. According to some embodiments, a base-resolution image may have already been generated for a particular high-resolution image. In one embodiment, the server can be configured to generate a base-resolution image for each high-resolution image that is uploaded, input to, or generated on the server 120. In some embodiments, the resolution level of the base-resolution image can be configured based on the attributes of the client device upon which the base-resolution image is to be displayed. For example, server 120 can be configured to generate base-resolution image that has a lower resolution for a mobile device, such as a mobile phone, which typically have a smaller sized display while the server 120 may be configured to generate a base-resolution image that has a comparably higher resolution for display on a laptop or desktop computer system that has a larger display area having a higher resolution. The server 120 can then send the base-resolution image to the client device 120 via network 130 (step 335).

The server 120 can then receive a request from the client device 110 for a full high-resolution image or a portion of the high-resolution image that corresponds to an area of interest (step 340). When a portion is requested, it may be the same size as what will be displayed in the virtual lens 160 or larger. If access is to be restricted, determination can again be made whether the user or client device 110 (or both) has access rights to the image (step 345) per the access control policy. If the user does not have access to the image, the server 120 can be configured to send a message to the client device 110 indicating that the user does not have access to the requested content (step 360). Otherwise, the server 120 can generate or retrieve from memory a high-resolution image or a portion of a high-resolution image that corresponds to the area of interest identified in the request (step 350) from an image of greater than or equal resolution generated on, input to, or stored on the server. In an embodiment, the resolution of the high-resolution image can be equal to the maximum resolution of the image that is stored on, generated on, or input to the server 120 or the resolution of the high-resolution image can be less than the resolution of the maximum-resolution image stored on, generated on, or input to the server 120 but greater than the resolution of the base-resolution image that was provided to the client in step 335. The server 120 can then transmit the high-resolution image generated in step 350 to the client device 110 via the network 130 (step 355). According to some embodiments, the request that is received from the client device 110 can specify a level of resolution to be used for the portion of the high-resolution image generated in step 350. For example, an application being executed on the client device 110 that has requested a high-resolution image can include a user interface that include a "zoom" tool that allows the user to select a level of resolution of the high-resolution image to be displayed in the virtual lens 160. In some embodiments, server 120 can cache the high-resolution images that are generated in response to client requests so that the server 120 does not have to generate the high-resolution image again if another request is received for that image at that resolution level in the future.

According to some embodiments, various optimizations can be provided for the successive download method. For example, in some embodiments, images of multiple resolutions can be preloaded by the client device in anticipation of the user requesting to view those images. In another embodiment, images at different resolutions that the client has downloaded may be cached in memory. According to another embodiment, the client device 110 can be configured to request and the server 120 can be configured to transmit only that portion of a high-resolution image that will be displayed in the virtual lens, or a region from a high-resolution image containing the area to be displayed within the virtual lens, rather than the full high-resolution image. In one example, this approach can be used if the transmission times for the full high-resolution image are too high or if the user is expected to view only a subset of the image at high resolution.

In some embodiments, the resolution level of the base-resolution image can be determined based on the attributes of the client device 110 upon which the base-resolution image is to be displayed and the bandwidth and delay characteristics of the network 130 connecting the client device 110 and the server 120. For example, server 120 can be configured to generate base-resolution image that has a lower resolution for a mobile device, such as a mobile phone, which typically have a smaller sized display while the server 120 may be configured to generate a base-resolution image that has a comparably higher resolution for display on a laptop or desktop computer system that has a larger display area having a higher resolution. In an embodiment, the resolution level of the high-resolution images corresponding to the base-resolution image can also be adjusted based on the attributes of the client device 110, the server 120, and the network 130.

Client Downscaling Method

Figure 5:
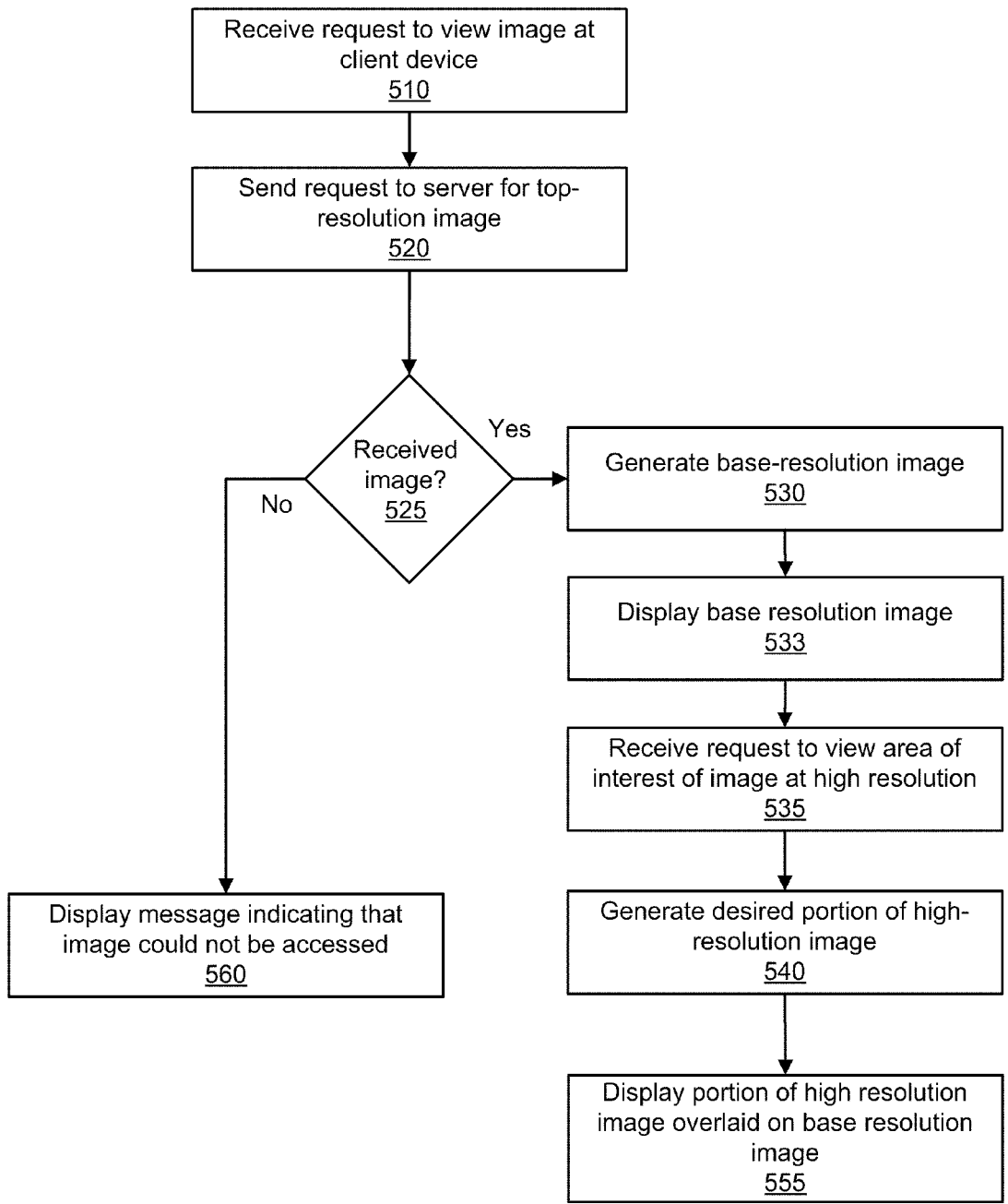
FIG. 5 is a flow diagram of a client downscaling method that can be implemented on a client device of the image viewing system illustrated in FIG. 1 according to an embodiment.
Figure 6:
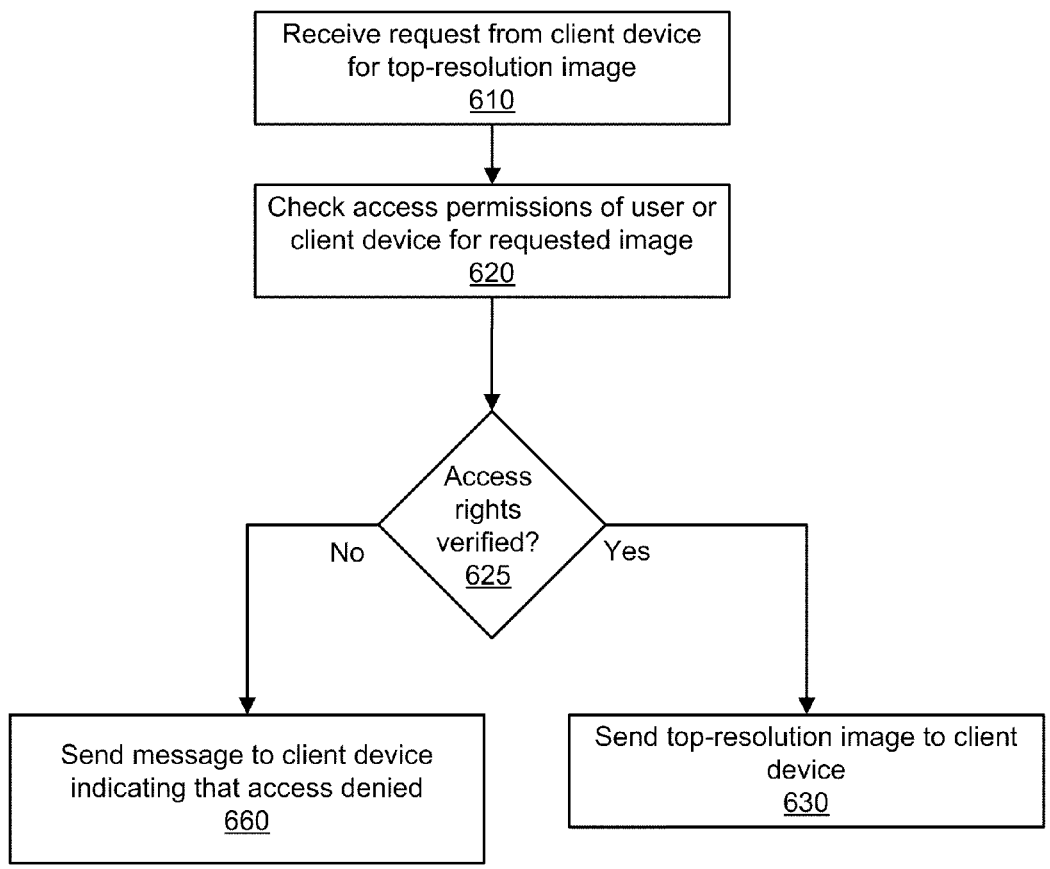
FIG. 6 is a flow diagram of a client downscaling method that can be implemented on a server of the image viewing system illustrated in FIG. 1 according to an embodiment.

FIGS. 5 and 6 are flow diagrams of a client downscaling method that can be used in conjunction with an image viewing system 100 according to an embodiment. FIG. 5 illustrates the steps of the method that can be performed at client device 110 according to one embodiment, and FIG. 6 illustrates the steps of a method that can be performed by server 120.

The method of FIG. 5 begins when a client device 110 receives a request to view an image at the client device (step 510). The client device 110 sends a request to the server 120 for a top-resolution image (step 520) that corresponds to the image that was requested, where the requested top resolution is less than or equal to the maximum resolution at which the image is generated on, input to, or stored in memory on the server 120. According to an embodiment a display engine module can be implemented on the client device 110 that is configured to process requests for images from applications on the client device 110 and to send a request via network 130 to the server 120 for a top-resolution image that corresponds to the requested image.

A determination is made whether the top-resolution image was received from the server 120 (step 525). According to an embodiment, if access to the image is to be restricted, the server 120 can make a determination whether the user of the client device or client device 110 (or both) is authorized to view the image content requested per the access control policy. According to an embodiment, the request sent by the client device 110 can include identification information associated with a user or the client device 110 that can be used to determine whether the server 120 should grant access to the image content stored on, generated on, or input to the server 120. If the user or client device 110 is not authorized to access the requested image, the server 120 can optionally send a message to the client device 110 indicating that the user or client device 110 is not authorized to access the requested image. According to an embodiment, the client device 110 can also be configured keep track of how much time has passed since the request was transmitted to the server 120 and to timeout the request if the top-resolution image is not received within a predetermined amount of time.

If the image is not received from the server 120, the client device 110 can optionally display a message to the user indicating that the requested image could not be accessed (step 560). According to some embodiments, a detailed error message can be generated that describes why the image could not be accessed. For example, the message can indicate that the request timed out if a response was not received within a predetermined amount of time, or that the user was not authorized to view the requested content.

If the image is received by the client device 110 from the server 120, the client device 110 can generate a base-resolution image (step 530) from the top-resolution image received from the server 120. According to an embodiment, the display engine of the client device 110 can be configured to scale down the top-resolution image upon receipt of the image from the server 120. According to an embodiment, the display engine can be configured to scale down the top-resolution image based on the available display space.

According to some embodiments, a base-resolution image may have already been generated by the client device 110 for a particular top-resolution image that was previously received from server 120. In some embodiments, the resolution level of the top-resolution image can be configured based on the attributes of the client device upon which the image is to be displayed and/or the bandwidth and delay characteristics of the network 130 connecting the client device 110 and the server 120. For example, server 120 can be configured to generate a top-resolution image that has a lower resolution for a mobile device, such as a mobile phone, which typically have a smaller sized display while the server 120 may be configured to generate a top-resolution image that has a comparably higher resolution for display on a laptop or desktop computer system that has a larger display area having a higher resolution.

The client device 110 can display the base-resolution image in display region 150 of the client device 110 (step 533). According to an embodiment, the display engine of the client device can be configured to adjust the size of the base-resolution image based on the available space on the display area of the client device 110 for displaying the base-resolution image. The client device 110 can then receive a request from the user to view an area of interest of the image in high resolution (step 535). According to an embodiment, the user can use an input device, such as a pointing device, including a mouse, touch pad, touch screen, joystick, track ball, arrow keys, buttons or other input device that allows the user to select an area of interest within the base-resolution image that the user would like to view in high resolution. According to an embodiment, the client device 110 can provide a user interface where the user can drag or move a cursor or a shape, such as a rectangle or oval, to the location of the area of interest on the base-resolution image.

The client device 100 can then generate a high-resolution image that corresponds to the area of interest identified by the user (step 540). The client device can generate the high-resolution image from the top-resolution image that was received from the server 120. According to an embodiment, when the user requests to view an area of interest within the image at a high resolution (higher than the resolution of the base-resolution image), the client device 110 can scale down the top-resolution image to a high-resolution image of higher resolution than the base resolution (e.g., 1080×810 for a 720×540 base resolution) and display the portion of the high-resolution image in the virtual lens 160 corresponding to the area of interest selected by the user (step 555). The virtual lens 160 overlays the area of interest in the underlying base-resolution image. According to an embodiment, if the user requests a still higher resolution image, the display engine generates another high-resolution image of higher resolution than the previous high-resolution image of a resolution up to and including the top resolution received from server 120, and displays a portion of that high-resolution image in the virtual lens 160 corresponding to the user-selected area of interest. Once again, the virtual lens 160 can be overlaid on the area of interest in the underlying base-resolution image. Further, in some embodiments, the display engine module can be configured to provide a user interface that allows a user to request changes in the virtual lens size as well as in the resolution of the image displayed by the virtual lens 160.

The method illustrated in FIG. 6 illustrates the steps taken by the server 120 that correspond to the steps performed by the client device 110 in FIG. 5. The server 120 receives a request for a top-resolution image from the client device 110 (step 610). If access to the image is to be restricted, the server 120 can check whether the user or client device 110 has access rights to the requested image (step 620) per an access control policy. According to an embodiment, the request sent by the client device 110 can include identification information associated with a user or the client device 110 that can be used in determining whether the server 120 should grant access to the image content stored on, generated on, or input to the server 120.

A determination is made whether the user or client device 110 has access rights for the requested image (step 625). If the user does not have access rights for the requested image, the server 120 can optionally be configured to send a message to the client device 110 indicating that the user or client device 110 does not have access to the requested content (step 660). Otherwise, if the user has access to the requested image, the server 120 can generate a top-resolution image from an associated high-resolution image of greater than or equal resolution that was generated on, input to, or stored on the server 120, and transmit the top-resolution image to the client device 110 via the network 130 (step 630).

Various optimizations may be provided for the client downscaling method, including preloading the top-resolution images on the client device 110 in anticipation of the user requesting to view these images (e.g., if the image is the next in a series of different images to be viewed).

The client downscaling method can be used in conjunction with the successive download method. For example, in one embodiment, for up to a particular resolution, the client downscaling method could be used. For requests for high-resolution images above that resolution threshold, the successive download method can be used. In this case, the top-resolution image downloaded for the client downscaling method can be of lower resolution than the maximum available on the server. Alternatively, the successive download method can be used up to a particular resolution, and the client downscaling method used above the predetermined resolution threshold. In some embodiments, a combination of the two methods can be used to optimize various performance parameters for certain usage scenarios.

Server Composition Method

Figure 7:
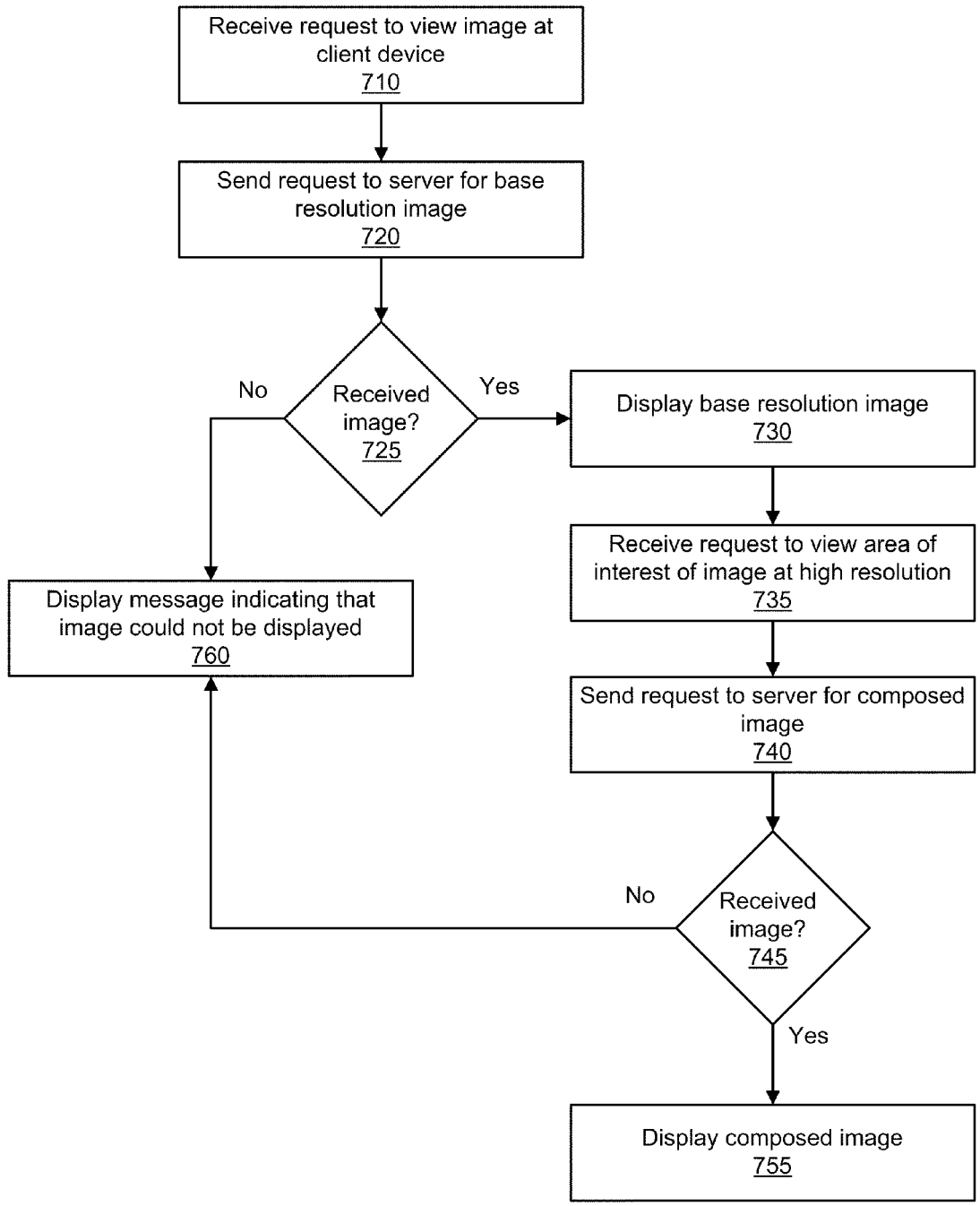
FIG. 7 is a flow diagram of a server composition method that can be implemented on a client device of the image viewing system illustrated in FIG. 1 according to an embodiment.
Figure 8:
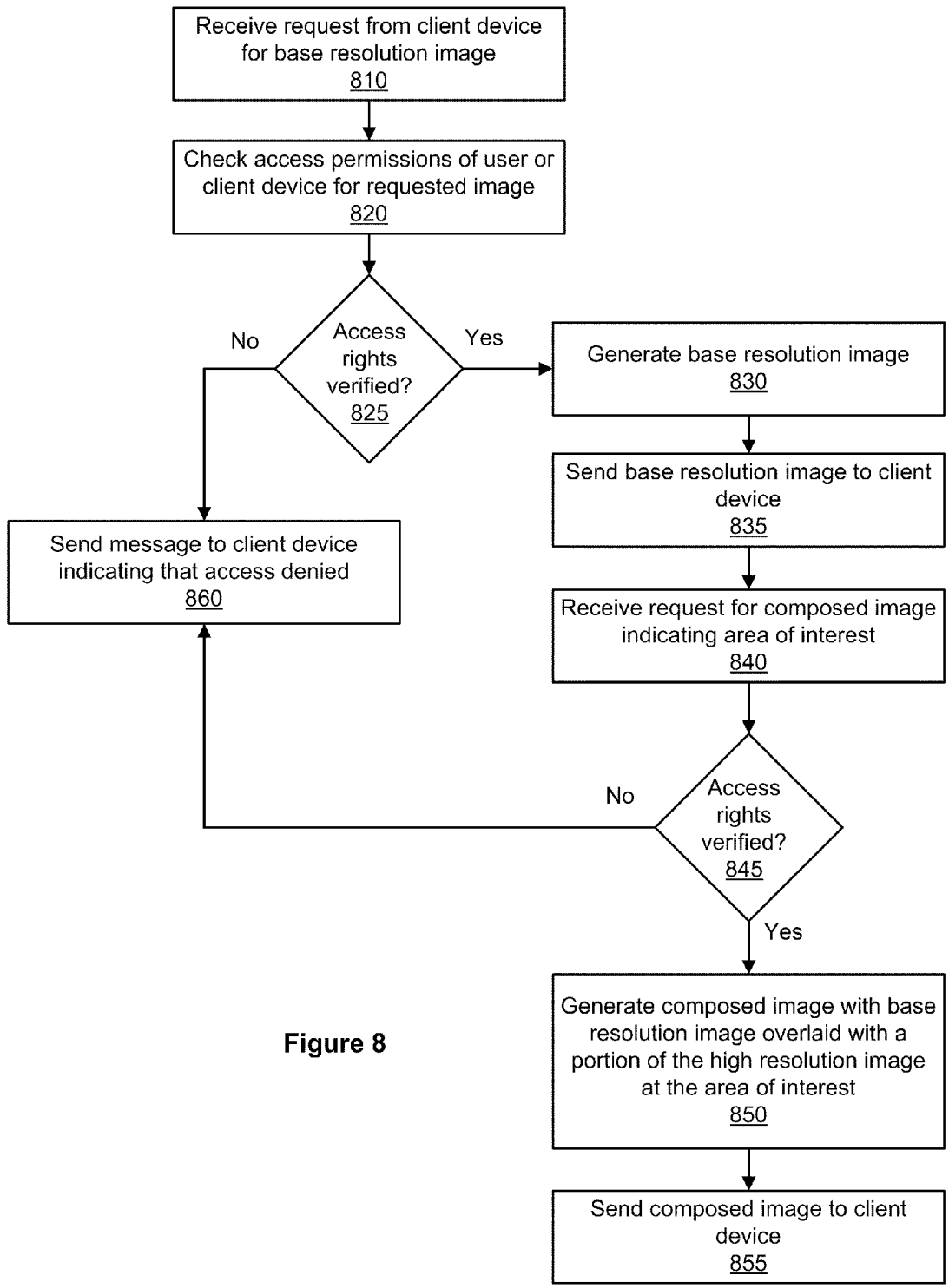
FIG. 8 is a flow diagram of a server composition method that can be implemented on a server of the image viewing system illustrated in FIG. 1 according to an embodiment.

FIGS. 7 and 8 are flow diagrams of a server composition method that can be used in conjunction with an image viewing system 100 according to an embodiment. FIG. 7 illustrates the steps of the method that can be performed at client device 110 according to one embodiment, and FIG. 8 illustrates the steps of a method that can be performed by server 120.

The method of FIG. 7 begins when a client device 110 receives a request to view an image at the client device (step 710). According to an embodiment, the request can comprise a user accessing a document or image from an application. In other embodiments, the request can comprise a user accessing a particular web page or other content from a browser application running on the client device 110. In yet another embodiment, the request can comprise a user executing an application on the client device 110 that uses high-resolution image content retrieved from the server 120.

In the example of FIG. 7, the client device 110 sends a request to the server 120 for a base-resolution image (step 720) that corresponds to the image that was requested. According to an embodiment, a display engine module can be implemented on the client device 110 that is configured to process requests for images from applications on the client device 110 and to send a request via network 130 to the server 120 for a base-resolution image that corresponds to the requested image.

A determination is made whether the image was received from the server 120 (step 725). According to an embodiment, if access to the image is to be restricted, the server 120 can make a determination whether the user of the client device or client device 110 (or both) is authorized to view the image content requested per the access control policy. According to an embodiment, the request sent by the client device 110 can include identification information associated with a user or the client device 110 that can be used in determining whether the server 120 should grant access to the image content stored on, generated on, or input to the server 120. If the user is not authorized to access the requested image, the server 120 can optionally send a message to the client device 110 indicating that the user or client device 110 is not authorized to access the requested image. According to an embodiment, the client device 110 can also be configured to keep track of how much time has passed since the request was transmitted to the server 120 and to timeout the request if the base-resolution image is not received within a predetermined amount of time.

If the image is not received from the server 120, the client device 110 can optionally display a message to the user indicating that the requested image could not be accessed (step 760). According to some embodiments, a detailed error message can be generated that describes why the image could not be accessed. For example, the message can indicate that the request timed out if a response was not received within a predetermined amount of time, or that the user was not authorized to view the requested content.

If the image is received by the client device 110 from the server 120, the client device 110 can display the base-resolution image in display region 150 of the client device 110 (step 730). According to an embodiment, the display engine of the client device can be configured to adjust the size of the base-resolution image based on the available space on the display area of the client device 110 for displaying the base-resolution image.

The client device 110 can then receive a request from the user to view an area of interest of the image in high resolution (step 735). According to an embodiment, the user can use an input device, such as a pointing device, including a mouse, touch screen, touchpad, joystick, trackball, arrow keys, buttons, or other input device that allows the user to select an area of interest within the base-resolution image that the user would like to view in high resolution.

The client device can then send a request to the server 120 for a composed image comprised of the base-resolution image overlaid at the area of interest with a virtual lens showing the area of interest in high-resolution image (step 740). According to an embodiment, the request can include the coordinates of the area of interest relative to a reference point on the image, the desired resolution level for the high-resolution image, and the virtual lens size and shape. The desired resolution can fall into a range above the resolution of the base-resolution image and up to the resolution of the maximum-resolution image stored on, generated on, or input to the server 120. One or more areas of interest may be specified, each at a specified position, resolution, and virtual lens size and shape.

According to an embodiment, the request can include a set of coordinates relative to a reference point on the base-resolution image that correspond to the area of interest. For example, in some embodiments, the client device 110 is configured so that a user can draw a rectangle on the base-resolution image to indicate the area of interest that the user would like to see in high resolution, and coordinates of the left-top and right-bottom corners of the rectangle, or the coordinates of the left-top and the width and height of the rectangle, can be provided to the server 120 in the request for the high-resolution image. According to an embodiment, the display engine module can be configured to translate screen coordinates to pixel coordinates on the base-resolution image, and the request to the server for the high-resolution image can include the pixel coordinates of the area of interest specified by the user. According to an alternative embodiment, the client device 110 can provide a user interface where the user can drag or move a cursor or shape, such as a rectangle or oval, to the location of an area of interest on the base-resolution image in order to receive a high-resolution image that corresponds to the area indicated by the cursor or covered by the shape.

A determination is made whether the composed image was received from the server 120 (step 745). If the image is not received from the server 120, the client device 110 can optionally display a message to the user indicating that the requested image could not be accessed. Otherwise, if the requested composed image is received by the client device 110, the client device 110 can replace the high-resolution image in display region 150 with the composed image (step 755).

According to an alternative embodiment, in order to improve response time, the composed image can be downloaded from the server 120 in advance of a user's request to view the portion of the high-resolution image in the virtual lens 160. In such an embodiment, the composed image is not displayed until such display is requested by the user. According to an embodiment, the pre-fetch of the composed image can be initiated by some user action, which can trigger the client device 110 to send a request the server 120 for the composed image. For example, in some embodiments, the download of the composed image can be requested at the time the base-resolution image is requested from the server 120, or shortly after the base-resolution image is received from the server. Such requests can be sent if the area of interest can be determined in advance of the user actually requesting that portion of the image. For example, when a route on a map is displayed, the areas of interest may be the origin and destination. More than one such image can be pre-fetched for different areas of interest or different high resolution levels. Alternatively, in other embodiments, the client device 110 can be configured to initiate the download of the composed image with an anticipated area of interest and initial high resolution level in response to the user depressing a soft or hard key (e.g., an "image viewing system activate" button) or by clicking on a pointing device button or other button or key. Continuing this pre-loading technique, a subsequent download of the composed image with the next higher resolution displayed in the virtual lens can be requested upon completion of each composed image download, up to the maximum resolution.

According to an embodiment, the client device 110 can be configured to allow the user to move the virtual lens 160 over the base-resolution image in display region 150. In one embodiment, the client device 110 is configured such that the user can move the virtual lens using a pointing device, such as mouse, touchpad, touch screen, joystick, trackball, arrow keys, or buttons. In an embodiment, the display engine module of the client device 110 is configured to request from the server 120 in real time, as the user moves the cursor across the base-resolution image, the composed image for the area of interest indicated by the current cursor position relative to a reference point on the base-resolution image, at the same resolution level and virtual lens size and shape. When the new composed image is received, the client device 110 can display the new composed image in place of the previously received composed image. With the server composition method, the ability to track the cursor movement and change the area of interest and virtual lens location and contents accordingly relies on a high bandwidth, low latency network 130 and a responsive server 120. According to an embodiment, the display engine takes into account the cursor position within the base-resolution image relative to a point of reference, such as the left-top corner of the image, to determine the coordinates of the area of interest. In an embodiment, the display engine module can also take into account whether the user has scrolled the display on the client device display and adjust for horizontal or vertical scrolling amounts (or both).

According to an embodiment, the display engine module of the client device 110 can be configured to allow a user to request a change in the level of resolution of the high-resolution image displayed in the virtual lens 160. According to an embodiment, the display engine module can be configured to provide user interface controls, such as soft buttons, sliders, pointer device controls, or other types of interface components with which the user can interact to select a desired level of resolution for the high-resolution image displayed in the virtual lens 160. In an embodiment, the user can select a level of resolution for the image displayed in the virtual lens 160 that is up to the maximum resolution level of the image stored on, generated on, or input to the server 120. In an embodiment, the user can select a level of resolution that is up to the maximum resolution and greater than the resolution of the base-resolution image.

In response to a request to change the resolution of the portion of the image displayed by the virtual lens 160, the display engine module can be configured to send a request to the server 120 for the composed image comprised of the base-resolution image overlaid at the area of interest with a virtual lens containing the portion of the high-resolution image corresponding to the area of interest at the selected resolution level.

According to an embodiment, the display engine of the client device 110 can also be configured to allow a user to change the size of the virtual lens 160 as well as the resolution of the image displayed by the virtual lens 160. According to an embodiment, the display engine can provide controls that comprise soft buttons (buttons or other interface components drawn on the client device display and selected with the pointing device), hard buttons (keyboard or other buttons or switches), or pointer device controls (e.g., left or right mouse button clicks, mouse button down or up, track wheel controls, track ball controls, touch-sensitive controls, or other pointer device controls). According to an embodiment, the display engine can also be configured to provide controls that enable a user to freeze the virtual lens at its current position (i.e., stop it from tracking the pointing device movement), or unfreeze the virtual lens (resume tracking the pointing device movement). According to an embodiment, the display engine can also be configured to provide controls that enable a user to turn off the virtual lens display, such that the full base-resolution image is shown without the high resolution overlay, or to turn the virtual lens display back on. Some controls can perform multiple functions, such as changing both the virtual lens size and resolution of the image displayed by the virtual lens 160. For any change to the virtual lens 160 size or position, or change to whether the virtual lens 160 is shown or hidden, the client device 110 can send a request to the server 120 for new composed image, unless a matching composed image is already in client device's 100 memory. When the composed image is received, client device 110 can display the composed image in place of the previous composed image.

The method illustrated in FIG. 8 shows the steps taken by the server 120 that correspond to the steps performed by the client device 110 in FIG. 7. The server 120 receives a request for a base-resolution image from the client device 110 (step 810). If access is to be restricted, the server 120 can check whether the user or client device 110 (or both) has access rights to the requested image (step 820) per an access control policy. According to an embodiment, the request sent by the client device 110 can include identification information associated with a user or the client device 110 that can be used in determining whether the server 120 should grant access to the image content stored on, generated on, or input to the server 120.

A determination is made whether the user has access rights for the requested image (step 825). If the user does not have access to the requested image, the server 120 can be configured to send a message to the client device 110 indicating that the user does not have access to the requested content (step 860). Otherwise, if the user or client device 110 has access to the requested image, the server 120 can generate a base-resolution image (step 830) from the high-resolution image stored on, generated on, or input to the server 120. According to some embodiments, a base-resolution image may have already been generated for a particular high-resolution image. In one embodiment, the server can be configured to generate a base-resolution image for each high-resolution image that is uploaded, input to, or generated on the server 120. In some embodiments, the resolution level of the base-resolution image can be configured based on the attributes of the client device upon which the base-resolution image is to be displayed. For example, server 120 can be configured to generate base-resolution image that has a lower resolution for a mobile device, such as a mobile phone, which typically have a smaller sized display while the server 120 may be configured to generate a base-resolution image that has a comparably higher resolution for display on a laptop computer system that has a larger display area having a higher resolution. The server 120 can then send the base-resolution image to the client device 120 via network 130 (step 835).

The server 120 can then receive a request from the client device 110 for a composed image, including the coordinates of the area of interest, resolution levels of the base-resolution image and high-resolution overlay, and virtual lens size and shape (step 840). If access is to be restricted, determination can again be made whether the user or client device 110 has access rights to the image (step 845) per the access control policy. If the user does not have access to the image, the server 120 can be configured to send a message to the client device 110 indicating that the user does not have access to the requested content (step 860). Otherwise, the server 120 can generate or retrieve from memory a composed image comprised of the base-resolution image overlaid at the area of interest with a virtual lens containing the portion of a high-resolution image that corresponds to the area of interest identified in the request (step 850). In an embodiment, the resolution of the high-resolution image can be equal to the maximum resolution of the image that is stored on, generated on, or input to the server 120 or the resolution of the high-resolution image can be less than the resolution of the maximum-resolution image stored on, generated on, or input to the server 120 but greater than the resolution of the base-resolution image that was provided to the client in step 835. The server 120 can then transmit the composed image generated in step 850 to the client device 110 via the network 130 (step 855). According to some embodiments, the request that is received from the client device 110 can specify a level of resolution to be used for the portion of the high-resolution image generated in step 350. For example, an application being executed on the client device 110 that has requested a high-resolution image can include a user interface that include a "zoom" tool that allows the user to select a level of resolution of the high-resolution image to be displayed in the virtual lens 160. In some embodiments, server 120 can cache the composed images that are generated in response to client requests so that the server 120 does not have to generate the composed image again if another request is received for that image at that resolution level in the future.

According to some embodiments, various optimizations can be provided for the server composition method. For example, in some embodiments, composed images can be preloaded by the client device in anticipation of the user requesting to view those images. In some embodiments, the resolution level of the base-resolution image can be configured based on the attributes of the client device 110 upon which the base-resolution image is to be displayed and the bandwidth and delay characteristics of the network 130 connecting the client device 110 and the server 120. For example, server 120 can be configured to generate a base-resolution image that has a lower resolution for a mobile device, such as a mobile phone, which typically have a smaller sized display while the server 120 may be configured to generate a base-resolution image that has a comparably higher resolution for display on a laptop computer system that has a larger display area having a higher resolution. The resolution level of the high-resolution images corresponding to the base-resolution image may also be adjusted based on the attributes of the client device 110.

Collaborative Method

According to another embodiment, the image viewing system 100 can be configured to allow a first user to select an area of interest, resolution, and virtual lens shape and size on behalf of a second user or users. This technique can be employed, for example, in collaborative or instructional applications. In an embodiment, the first user's selection is saved for later use when the second user requests the image. The selection parameters can be communicated to the client device 110 of the second user for use in sending a request for the image to the server, or can be saved on the server 120 for use when the second user requests the image. With this technique, the second user can bypass the steps of selecting the area of interest, virtual lens size and shape, and resolution level of the high-resolution image displayed in the virtual lens since the selection has already been done by the first user. In an embodiment, this technique can be used in combination with either the successive download method, the client downscaling method, or the server composition method. Either of these methods can be used by the first user in specifying the selection parameters to be used by the second user. In another embodiment, the first user can enter the selection parameters via the client device, for example, using a menu or command. In an embodiment, either the successive download method, the client downscaling method, or the server composition method can be used by the second user, with the steps of selecting the area of interest, virtual lens size and shape, and resolution level of the high-resolution image replaced by the steps of retrieving or determining the selection parameters. Subsequently, the methods of the successive download method, the client downscaling method, or the server composition method can be used to, for example, move the virtual lens or change the virtual lens size and shape, or change the resolution of the high-resolution image displayed in the virtual lens. In an embodiment, collaboration can be done in real time, with the first user, for example, moving the virtual lens for the second user, or changing the resolution of the image displayed in the virtual lens for the second user, or changing the second user's virtual lens size or shape.

Figures 9A, 9B:
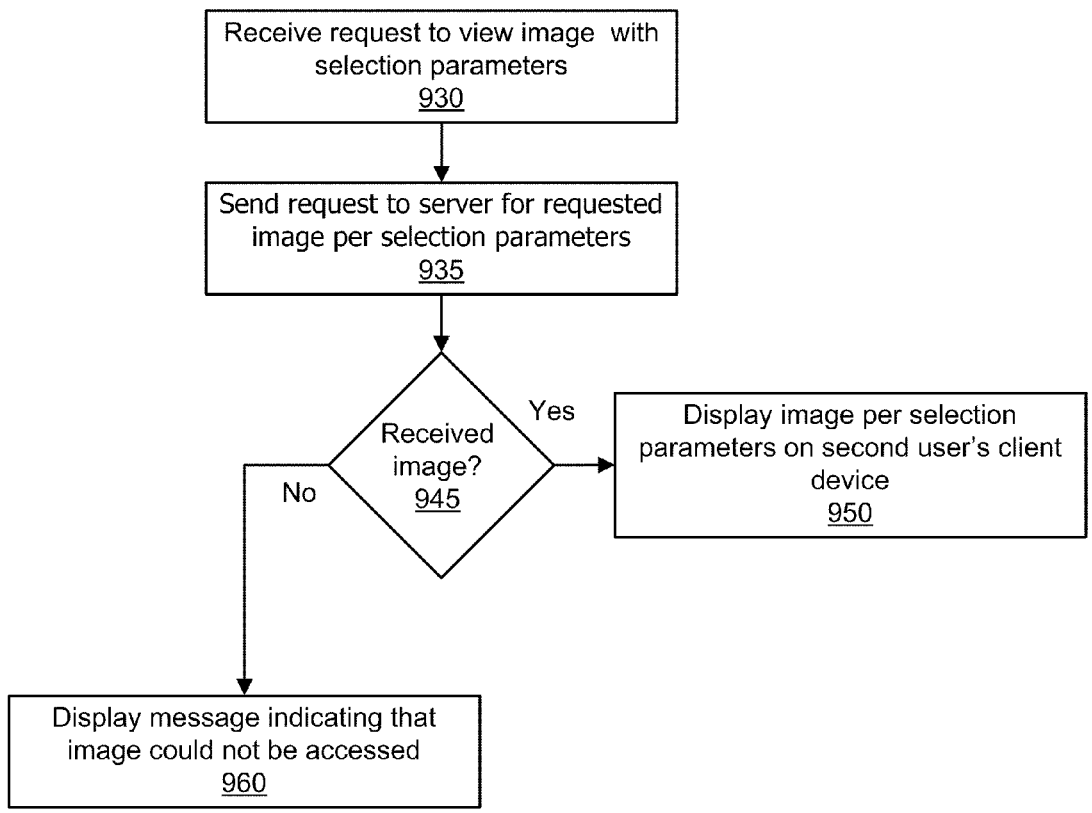
FIGS. 9A and 9B are flow diagrams of a collaborative method that can be implemented on client devices of the image viewing system illustrated in FIG. 1 according to an embodiment.

FIGS. 9A and 9B are flow diagrams of a collaborative method that can be implemented on client devices of the image viewing system illustrated in FIG. 1 according to an embodiment. FIG. 9A illustrates a method for specifying a set of selection parameters for displaying an image to a second user according to an embodiment. The selection parameters can include an area of interest, resolution specification, a virtual lens specification, other display parameters, or a combination thereof. The resolution specification can include the resolution of the base-resolution image and the resolution of the high-resolution image, or the ratio of the high resolution over the base resolution, or equivalent. A ratio can be used to enable the first user's client device and second user's client device to display the base-resolution image at different resolutions (e.g., when the displays are different sizes), and to display the portion of the high-resolution image on the second user's client device such that the proportional resolution increase of the high-resolution image over the base-resolution image matches that used by the first user. The virtual lens specification comprises a virtual lens shape and either a virtual lens absolute size or size relative to the size of the base resolution image.

A first user specifies the selection parameters to be used by the viewing system 100 for displaying an image to a second user (step 910). The first user can then transfer the selection parameters to the second user (step 920). According to an embodiment, the first user can transmit the selection parameters from the first user's client device 110 to the second user's client device 110. For example, for a web application, the first user can send the parameters in an email message that includes a Uniform Resource Locator (URL) link that includes the selection parameters in the query string. When the link is clicked by the second user, the email client in the second user's client device 110 passes the link to a browser, which can then request the web page that contains the logic to request the images specified in the selection parameters from the server 120 and render them on the second user's client device's display, with a portion of the high-resolution image corresponding to specified the area of interest displayed at the specified resolution in a virtual lens of the specified size and shape, overlaid over the base-resolution image at the area of interest. In an alternative embodiment, a first application running in the first user's client device 110 may transmit the selection parameters to a second application running in the second user's client device 110. In an alternative embodiment, an application running in the first user's client device 110 may transmit the selection parameters to the server 120 for retrieval and use by an application running on the second user's client device 110. In an alternative embodiment, the selection parameters can be computed by algorithms executing on either the first user's client device, second user's client device, or the server. The algorithms may be used in combination with user input. As an example embodiment, for mapping applications, an algorithm may locate a specific location on a map such as an origin or destination of a route. An algorithm can also permit a route to be traced in high resolution over a period of time or in response to user input. As another example, for a video, algorithms can be used to track a moving object over time in high resolution in the context of the base-resolution surroundings. The initial location of or characteristics of the object can be specified by the user.

FIG. 9B illustrates a method for receiving a set of selection parameters for displaying an image and requesting the image from the server 120 according to an embodiment. Client device 110 receives from the second user a request to view the image corresponding to the selection parameters (step 930). The second user can specify that the selection parameters be used in displaying the requested image, or logic executing on the second user's client device 110 can automatically determine that there are selection parameters for the image and process the image for display accordingly. The determination as to whether there are selection parameters can be performed either by whether the selection parameters have been received from the first user's client device, by querying the server for the selection parameters over the network, or by whether there is an algorithm that can be used on the second user's client device for generating them. The client device 110 then sends a request to the server 120 for the requested image (step 935). The request includes some or all of the selection parameters, depending on the method used. In an embodiment, for the successive download method, the client device 110 sends either separate requests or a combined request to the server 120 for the base-resolution image and the high-resolution image (or portion of the high resolution image). The client device 110 can determine the base resolution and high resolution levels from the selection parameters and the available display space on the client device's 110 display and the network 130 capabilities. When requesting a portion of the high-resolution image, the client device 110 includes the set of coordinates of a point or object in the area of interest relative to a reference point in the image, the resolution level of the high-resolution image, and the size and shape of the portion of the high-resolution image being requested. These parameters are derived from the selection parameters, possibly adjusted for the capabilities of the second user's client device 110 or the network 130 connecting the second user's client device 110 and the server 120. In an alternative embodiment, for the client downscaling method, the client device 110 sends a request to the server 120 for the top-resolution image. The top resolution level can be determined from the selection parameters and the capabilities of the client device 110 and the network 130. In an alternative embodiment, for the server composition method, the client device 110 sends to server 120 a request that includes the base resolution level, the high resolution level, the area of interest coordinates relative to a reference point, and virtual lens size and shape, all determined from the selection parameters and possibly modified to take into account the capabilities of the client device 110 and network 130.

A determination is made whether the requested image was received from the server 120 (step 945). According to an embodiment, if access to the image is to be restricted, the server 120 can make a determination whether the user of the client device or client device 110 (or both) is authorized to view the image content requested per the access control policy. According to an embodiment, the request sent by the client device 110 can include identification information associated with a user or the client device 110 that can be used to determine whether the server 120 should grant access to the image content stored on, generated on, or input to the server 120. If the user is not authorized to access the requested image, the server 120 can optionally send a message to the client device 110 indicating that the user or client device 110 is not authorized to access the requested image. According to an embodiment, the client device 110 can also be configured keep track of how much time has passed since the request was transmitted to the server 120 and to timeout the request if the requested image is not received within a predetermined amount of time.

If the image is not received from the server 120, the client device 110 can optionally display a message to the user indicating that the requested image could not be accessed (step 960). According to some embodiments, a detailed error message can be generated that describes why the image could not be accessed. For example, the message can indicate that the request timed out if a response was not received within a predetermined amount of time, or that the user was not authorized to view the requested content.

If the requested image or images are received by the client device 110 from the server 120, the client device 110 can display the requested image (step 950) using the selection parameters provided by the first user or algorithms. In an embodiment, when the second user is using the successive download method, client device 110 can receive a base-resolution image and a high-resolution image from the server 120. The client device 110 can display the base-resolution image overlaid with a portion of the high-resolution image corresponding to the area of interest at a location corresponding to the area of interest. In an embodiment, when the second user is using the client downscaling method, the client device 110 can receive the top-resolution image and use it to generate a base-resolution image and a high-resolution image. The client device 110 can then display the base-resolution image overlaid with the portion of the high-resolution image corresponding to the area of interest at a location corresponding to the area of interest. In an embodiment, when the second user is using the server composition method, the client device 110 can receive a composed image and display it.

Figure 10:
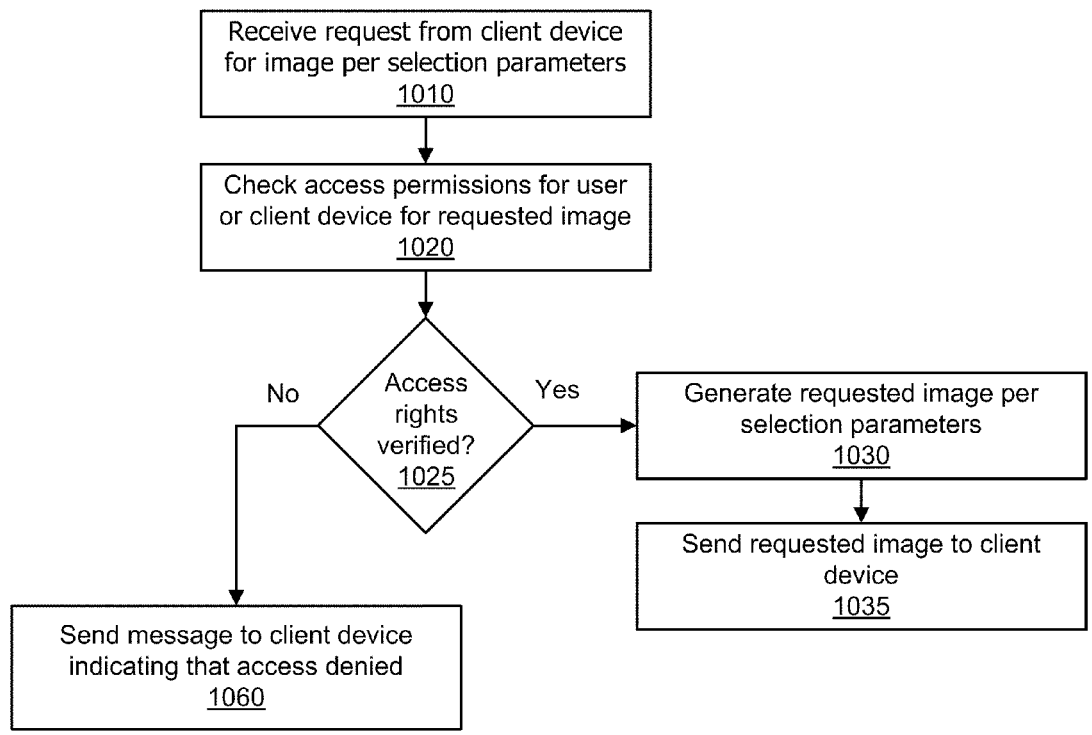
FIG. 10 is a flow diagram of a collaborative method that can be implemented on a server of the image viewing system illustrated in FIG. 1 according to an embodiment.

FIG. 10 is a flow diagram of a collaborative method that can be implemented on a server of the image viewing system illustrated in FIG. 1 according to an embodiment. The method illustrated in FIG. 10 illustrates the steps taken by the server 120 that correspond to the steps performed by the client device 110 in FIGS. 9A and 9B. The server 120 receives a request for a an image from the second user's client device 110 per the selection parameters (step 1010). If access to the image is to be restricted, the server 120 can check whether the second user or client device 110 has access rights to the requested image (step 1020) per an access control policy. According to an embodiment, the request sent by the client device 110 can include identification information associated with a user or the client device 110 that can be used in determining whether the server 120 should grant access to the image content stored on, generated on, or input to the server 120.

A determination is made whether the user or client device 110 (or both) has access rights for the requested image (step 1025) per an access control policy. If the user or client device 110 does not have access rights for the requested image, the server 120 can optionally be configured to send a message to the client device 110 indicating that the user does not have access to the requested content (step 1060). Otherwise, if the user has access to the requested image, the server 120 can generate the requested image or images based on the selection parameters (step 1030), and transmit them to the client device 110 via the network 130 (step 1035). In an embodiment, for the successive download method, the request can be for a base-resolution image, a high-resolution image or a portion of the high-resolution image, or both a base-resolution image and a high-resolution image or a portion thereof. The server 120 can generate and transmit the requested images to the client device 110. In an alternative embodiment, for the client downscaling method, the request can be for a top-resolution image, and the server 120 can generate and transmit to the client device 110 the top-resolution image of a resolution less that or equal to maximum resolution generated on, input to, or stored on the server 120. In an alternative embodiment, for the server composition method, the request can include selection parameters possibly adjusted to reflect the capabilities of the client device 110 and network 130, and the server 120 can compose an image per the selection parameters and transmit it to the client device 110.

According to another embodiment, the area of interest and other selection parameters may be selected for a user by an algorithm or algorithms executing on either the client device 110 or server 120. Examples include, for maps, the origin or destination of a route and, for medical images, a specific anatomical feature or abnormality.

Additional Methods

Other additional methods can optionally be used in combination with the Successive Download Method, the Client Downscaling Method, the Server Composition Method, and the Collaborative Method described above. Some examples of these methods are described below.

According to an embodiment, a method for preventing the virtual lens 160 from extending over the border of the base-resolution image is provided. In the methods described above, the display engine module of the client device 110 centers the virtual lens and the portion of the high-resolution image that is displayed by the virtual lens over the area of interest in the base-resolution image selected for high-resolution display. In an embodiment, the display engine module of the client device 110 can be configured to determine whether the virtual lens 160 would extend over the border of the base-resolution image and to offset the position of the virtual lens and the high-resolution image displayed by the virtual lens by the amount that the virtual lens would extend over the border of the base-resolution image. In one embodiment, the display engine of the client device 110 can adjust the size and shape of the virtual lens and offset the position of the virtual lens 160 in order to improve the function of an application in which the virtual lens 160 is being used. For example, the virtual lens can be positioned over an underlying newspaper or journal column in an electronic reader application, and the display engine can be configured to keep the virtual lens 160 centered over the column as long as the user keeps the pointer/cursor somewhere within the column.

According to another embodiment, the virtual lens can have a border, demarcating the virtual lens from the underlying base-resolution image. The types of border can include a line of various styles, thicknesses and colors, multiple lines of various styles, thicknesses and colors, a bevel, or other type of edge. As an alternative type of border for the virtual lens, the portion of the image at the edges of the virtual lens can be reduced in size and resolution such that the transition between the high resolution image displayed in the virtual lens and the base resolution image is smoother and there is less loss or no loss of a portion of the image due to the size differences between the high-resolution and base-resolution images. In such an embodiment, the virtual lens can appear as a type of bubble or raised area over the base-resolution image, the bubble or raised area having a relatively flat center section and edges curved in the third dimension (above the image). Some curvature distortion of the image would appear in the portions curved in the third dimension.

According to another embodiment, the display engine can be configured to freeze, upon user request, the position of and area of interest displayed in high resolution within the virtual lens 160, such that the virtual lens does not automatically track the movement of the pointing device. The display engine can also be configured to unfreeze the virtual lens 160 upon user request, such that the virtual lens position and contents automatically track the movement of pointing device.

According to another embodiment, the display engine can be configured to increase or decrease the size of the virtual lens 160, to change the shape, dimensions, or border of the virtual lens, change the accessories displayed with the virtual lens, increase the resolution of the image displayed by the virtual lens 160 up to the maximum resolution stored on, generated on, or input to the server, decrease the resolution displayed within the virtual lens down to but not including the base resolution, or a combination thereof. When the virtual lens size is increased or shape is changed, if the portion of the high-resolution image that is in the client device's 110 memory is insufficient to fill the virtual lens, the client device 110 can request from the server 120 a portion of the high-resolution image that is sufficiently large.

The display engine can also be configured to change both the resolution displayed within the virtual lens and the virtual lens size together upon user request. Further, the display engine can be configured to, upon user request, hide the virtual lens or show a previously hidden virtual lens. Additionally, for example, for video images or other images changing in time, the display engine can be configured to change the image displayed at base resolution in time according to the frame rate of the video content or the image changes of the time-changing content and to change the image displayed at high resolution in the virtual lens to be synchronized with the changing base-resolution image. In an embodiment, the frame rates and the current displayed frames of the base resolution video content and the high-resolution video content displayed in the virtual lens can be synchronized so that the virtual lens displays a high-resolution portion of the video content that is synchronized with the base resolution video content.

According to another embodiment, the image viewing system 100 can be configured to save a user's selection of area of interest for an image, the virtual lens shape and size, and the resolution displayed in the virtual lens. These parameters may be saved for a user either on the server 120 or the client device 110 for later retrieval and use.

Methods can be used to handle various performance situations or timing conditions. The display engine can be configured to provide an indication to the user in the situation that the high-resolution image to be displayed within the virtual lens has not completed downloading from the server over the network. Additionally, the display engine can be configured to internally represent the display in planes, with the virtual lens on top of the base image, and to compute the image to be displayed from these planes. For example, the display engine module can be configured to insert, when the virtual lens is not hidden, an additional opaque plane between the virtual lens and the underlying base image. This opaque plane can be of size and shape equal to the virtual lens and positioned immediately below the virtual lens. The display engine module can be configured to render the opaque plane as visible while there is no image to display in the virtual lens' plane, for example, when the high-resolution image has not completed downloading from the server.

According to an embodiment, the image viewing system 100 is capable of supporting a plurality of images. The image viewing system 100 can be configured to support a plurality of client devices 110 and client device users, each viewing possibly different images. The image viewing system 100 can include a plurality of servers 120. Multiple servers 120 can be used for load balancing purposes to increase performance and for failover in the event that a server fails or network connectivity to a server is disrupted. The image viewing system 100 can be configured to support a plurality of networks 130, for load sharing or failure protection. The detection of failures and the failover response can either be performed by the client devices 110, servers 120, or networks 130. The image viewing system 100 can be configured to support a plurality of virtual lenses 160 overlaid on the same base-resolution image in display region 150. The image viewing system 100 can be configured to support a plurality of base resolution images displayed on different regions of the client device's 110 display, each with one or more virtual lenses 160 overlaid showing an area of interest in high resolution.

According to an embodiment, the image viewing system 100 can employ various security methods. For example, the image viewing system 100 can be configured to restrict public access to specified content on the server 120. As part of the access control enforcement, the server 120 can employ methods to authenticate the identity of the client device's user (e.g., through a logon procedure on client device 110 involving a username and password, security token, biometrics, asymmetric encryption methods, asymmetric encryption with digital certificate methods, symmetric encryption methods, one-way hash methods, or other user authentication methods), and/or the identity of the client device 110 (e.g., through a pass code, asymmetric encryption methods, asymmetric encryption with digital certificate methods, symmetric encryption methods, one-way hash methods, or other device authentication method). Whether or not access control enforcement is performed on the client device 110, the client device's 110 user, or both the client device 110 and the user is determined from the access control policy for the system. Authentication may be performed for a particular viewing session when a user first invokes the image viewing system 100 or another system invokes the image viewing system 100 on the user's behalf. After authentication is performed, the server 120 may assign a session identifier that is to be submitted with requests from the client device 110. For example, for a web application, the server can store a session identifier in a client device's 110 browser cookie store, and the browser can send the value of this cookie with requests sent to the server. According to an embodiment, the server can use the authenticated identity to verify the rights of the user and/or client device 110 to access a requested image. Identification information as well as the images themselves can be protected when transmitted over the network 130 using encryption (e.g. using Transport Layer Security [TLS], Internet Protocol Security [IPSec], or other security protocol or encryption method). In another embodiment, access control can be based on rules for determining access rights using information other than user or device identity (e.g., mandatory access control at a network or subnetwork level).

According to an embodiment, to improve transmission times across the network 130, images can be compressed prior to transmission from the server 120 over the network 130 and decompressed on the client device 110. Compression can also be used to reduce the memory requirements on the server 120.

According to an embodiment, the display engine on the client device 110 can be configured to request an image at a specific resolution in anticipation of a user requesting to view the image at that resolution. Alternatively, the server 120 can be configured to transmit an image at a specific resolution or composition of resolutions to a client device 110 without an explicit request from the client device 110 for the image at the specified resolution or composition of resolutions, or without an explicit request for an update to an image that changes in time.

Example Embodiment

For illustrative purposes, an example embodiment of the image viewing system's successive download method is described below. One skilled in the art will recognize that there are numerous other ways of implementing the methods of this invention.

In this embodiment, the display engine in the client device can be comprised of a browser that renders a web page containing Hypertext Markup Language (HTML) or Extensible HTML (XHTML) elements, Cascading Style Sheet (CSS) declarations, and JavaScript code, downloaded from a web server. Other programming languages (e.g., Java, C#) can also be used instead of JavaScript.

In this embodiment, the region 150 of the client device's display in which the base-resolution image is displayed can be an HTML div element with an id of graphics0. The z-index property of the div element can be set to 0. The region of the display containing the virtual lens 160 can be a div with an id of graphics2. The z-index property of the virtual lens's div can be set to 2, and the div can have an outset border of 5 pixels in width. There is an additional opaque div with an id of graphics1 that lies between the virtual lens and the base-resolution image. The z-index property of this addition div can be set to 1, and is the same dimensions and size as the virtual lens. The graphics1 div can have an opaque background (e.g., a black background). A fourth div can also be positioned over the other three divs, with an id of graphics3. The fourth div can be the same size as the graphics0 div, and can be positioned exactly on top of graphics0, with a solid border, a transparent background, and null contents. All of these divs can be positioned using absolute coordinates on the page.

The user of the client device 110 can request to view an image using the user interface described above. The display engine module receives the request and can in turn send a request over the network to server 120 for the base-resolution image corresponding to the image requested by the user. Server 120 can authenticate the user to determine whether the user should have access to the requested content. In an embodiment, if the user has previously logged into the server, and the server has set a cookie containing a session identifier in the client device's 110 browser, the browser can send the session identifier in the cookie to the server over a TLS encrypted connection. If the user is permitted access, server 120 can transmit the base-resolution image to the client device 110, and the display engine module can display the base-resolution image in the graphics0 div (either in the foreground or in the background).

According to an embodiment, the user can request that the image viewing system be activated by clicking on a button displayed on the user interface of the client device 110. The display engine module can then establish a mousemove, mousedown, mouseover, and mouseout event handlers (or comparable touch screen event handlers) for the graphics3 div. The virtual lens can be assigned initial rectangular dimensions. The virtual lens width can be initialized to 50% of the width of the graphics0 div and the height can be initialized to 50% of the height of the graphics0 div. Code in the client device 110 then sends a request to the server for the image at a first high resolution. The server performs the access rights verification per the access control policy and, if the user is permitted access, transmits the high-resolution image to the client device 110.

While the high-resolution image is downloading, the display engine module can be configured to flash an indicator on the display indicating that the high-resolution image is being downloaded from the server. When the download completes, the display engine module can provide an indication to the user that the download is complete and the system is ready. Additionally, the display engine can change the cursor to indicate "wait" (e.g., the hour glass on a PC) while the download is taking place, and back to normal after it completes. After the download completes, the display engine module sends a request to the server 120 for the image at the next higher resolution (if there is one) in anticipation of the user requesting to view the next higher resolution image.

The user can click on an area of interest in the base image using a pointing device to request that a virtual lens containing a portion of the image at high resolution be displayed over the area of interest. The display engine can compute the position on the display where the virtual lens will be placed. In an embodiment, the virtual lens is centered over the center point of the area of interest, except when such centering would make the lens overlap the border of the graphics0 div. In such a situation, the virtual lens can be offset by the amount necessary to prevent such an overlap, making the point that corresponds to the center of the area of interest offset from the center of the virtual lens. The display engine module can then compute the position within the high-resolution image of the possibly offset area of interest, determining the left-top position within the high-resolution image. The display engine module puts the additive inverse of these coordinates in the graphics2 div style background position property. The display engine module can also set the left-top position of the graphics2 div to the absolute position of the virtual lens on the page. The display engine module can then load the high-resolution image into the background of the graphics2 div. The display engine module can also set the left-top position of the graphics1 div to match that of the graphics2 div. While the high-resolution image is loading, the opaque background of graphics1 div will appear at the virtual lens location.

When the user moves the cursor via the pointing device over the graphics3 div, the mousemove event handler can track the movement and cause both the virtual lens to change position and the portion of the high-resolution image shown within the virtual lens to be offset such that the point where the cursor is located in the high-resolution image displayed within the virtual lens matches the point in the underlying base image at the cursor position.

When the user left clicks on the pointing device, the display engine can freeze the virtual lens position. A subsequent left click can unfreeze the virtual lens position, and tracking of the cursor position resumes. This can be repeated indefinitely. Alternatively, when the user depresses the left mouse button, the display engine can unfreeze the virtual lens and then freeze the virtual lens position when the user releases the button. Similarly, for a touch screen, the display engine can unfreeze the virtual lens when the user touches it, and freeze it when the user stops touching it.

When the user right clicks on the pointing device, the display engine module can increase both the virtual lens size (graphics2 div and graphics1 div width and height) and the resolution displayed within the virtual lens. To do so, if the image at the next higher resolution has not yet downloaded, the display engine module can send a request for it to the server. Upon receipt of this request, server 120 verifies the access rights of the user per the access control policy, and if access is permitted, transmits the requested image to the client device over the network. The display engine can display a portion of this image in the virtual lens corresponding to the area of interest. In some embodiments, to improve performance, the display engine module can request the image at the next higher resolution as soon as the download of the current high-resolution image completes, so that downloading the image at the next resolution can overlap the user's inspecting of the image at the current resolution. If the download has not completed when the user requests the resolution, a loading indicator is displayed, the cursor is changed to "wait", and the opaque background from the graphics1 div can be shown at the virtual lens location. The display engine module can keep higher resolution images downloaded for a base image in a cache so that revisiting a resolution can be done without re-downloading image data.

The display engine can provide soft buttons on the display selected using the pointing device to increase or decrease the lens size (graphics2 div along with the underlying graphics1 div), increase or decrease the resolution displayed within the virtual lens, hide the virtual lens, and show the virtual lens.

The display engine module can automatically deactivate the image viewing system and virtual lens display when the user moves to another image or another activity.

Logical Architecture

Figure 11:
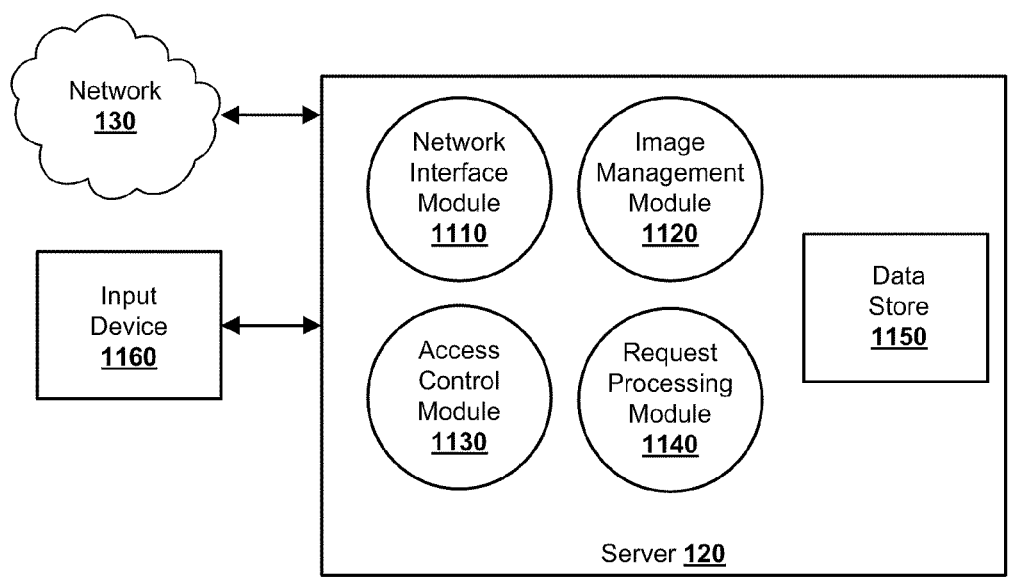
FIG. 11 is a block diagram of the logical components of a server illustrated in FIG. 1 according to an embodiment.

FIG. 11 is a block diagram of the logical components of the server 120 according to one embodiment. According to an embodiment, the server 120 can be used to implement the processes illustrated in FIGS. 3, 6, 8, and 10. The server 120 includes a network interface module 1110, an image management module 1120, an access control module 1130, and a request processing module 1140. The server 120 is also in communication with a data store 1150 that can be used to store image and/or video content for the server 120. In some embodiments, the data store 1150 can be a storage area that is implemented on the server 120 (as shown), while in other embodiments, the data store 1150 can be implemented on an external server or computer system that is in communication with the server 120 either directly or indirectly through a wired or wireless network connection.

Network interface module 1110 can be configured to receive requests for an image from the client device 110 over the network 130 and to transmit the requested image to the client device 110 via the network 130. The network interface module 1110 is configured to route incoming requests from the client device to the request processing module 1140 and to receive requested images from the request processing module 1140 for transmission to the client device 110. For the collaborative method, network interface module 1110 can be configured to receive selection parameters from a first user's client device 110, and store them in the data store 1150. Network interface module 1110 can also be configured to generate the selection parameters using algorithms. Network interface module 1110 is further configured to receive a request for selection parameters from a second user's client device 110, retrieve the requested selection parameters from the data store 1150 or generate them using algorithms, and send the selection parameters to the second user's client device.

Image management module 1120 is configured to receive image management requests for an image (or other content, such as video content) stored in the data store 1150, to access the image stored in the data store 1150, and to provide the requested image to the requesting module. The image management module 1120 is also configured to input an image from an image input device or system 1160 and to store the image in the data store 1150.

Request processing module 1140 is configured to receive from client device 110 an image request via the network interface module 1110, to send an image management request to the image management module 1120 to retrieve an image or other content, such as video content, associated with the request, generate the requested image, and send the requested image to the network interface module 1110 for transmission to the client device 110. In an embodiment, when the successive download method is used, the request processing module 1140 can generate a requested base-resolution image, high-resolution image, or portion of a high-resolution image using an image retrieved from the image management module 1120 having a resolution greater than or equal to the resolution of the requested image. In an embodiment, when the client downscaling method is used, the request processing module 1140 can generate a top-resolution image from an image retrieved from the image management module 1120 having a resolution greater than or equal to the resolution of the requested top-resolution image. In an embodiment, when the server composition method is used, the request processing module 1140 can generate a base resolution image as with the successive download method. Request processing module 1140 can generate a composed image by either retrieving a base-resolution image and high-resolution image from the image management module 1120, or retrieving a top-resolution image and generating the base-resolution image and high-resolution image from it, and then overlaying a portion of the high-resolution image corresponding to the area of interest at a location in the base image corresponding to the area of interest. In some embodiments, the request processing module 1140 is configured to request verification of access rights of the client device 110 or the client device's 110 user (or both) from the access control module 1130 to determine whether the access is permitted per an access control policy before generating and sending the requested image to the network interface module 1110 for transmission to the client device 110.

Access control module 1130 can be configured to determine, if image access is restricted, whether access to the requested content is permitted per the access control policy. If access to the image is restricted, the access control module 1130 can determine whether client device's 110 user or client device 110 (or both) that is requesting access to the image has access rights per the access control policy. If the user or device does not have access to the requested image, the authentication module can optionally generate a message indicating that the user or device does not have access to the requested image. The request processing module 1140 can send an authorization request to the access control module 1130 to determine whether a user or user device has access to a requested image, and the access control module 1130 can send an authorization response to the request processing module 1140 that indicates whether the user or client device has access to the image.

Figure 12:
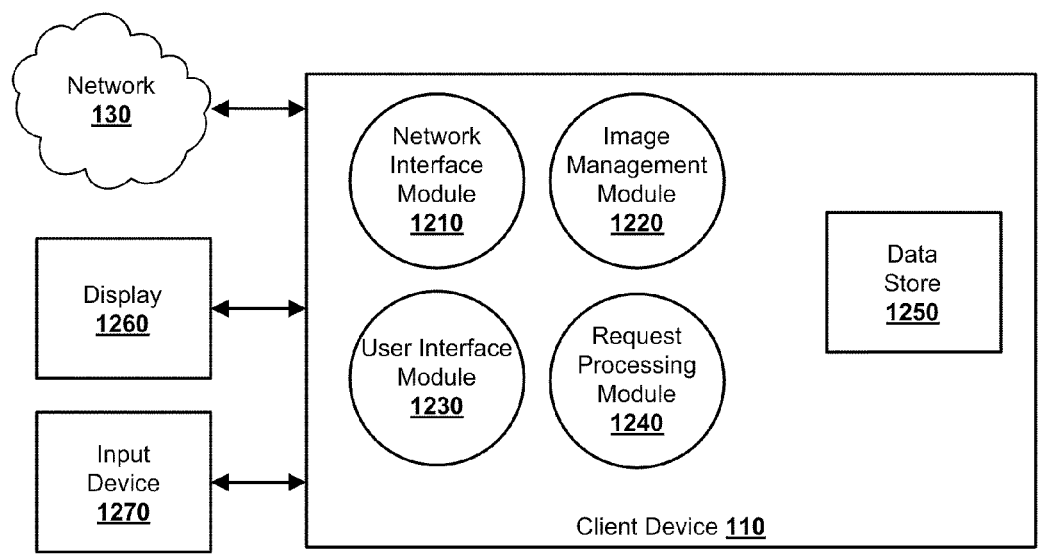
FIG. 12 is a block diagram of the logical components of the client device illustrated in FIG. 1 according to an embodiment.

FIG. 12 is a block diagram of the logical components of the client device 110 according to one embodiment. According to an embodiment, the client device 110 can be used to implement the processes illustrated in FIGS. 2, 5, 7, and 9. The client device 110 includes a network interface module 1210, an image management module 1220, a user interface module 1230, and a request processing module 1240. According to some embodiments, the client device 110 can also be in communication with a data store 1250 that can be used to store image and/or video content for the client device 110. In some embodiments, the data store 1250 can be a storage area that is implemented on the client device 110 (as shown), while in other embodiments, the data store 1250 can be implemented on an external server or computer system that is in communication with the client device 110 either directly or indirectly through a wired or wireless connection.

Network interface module 1210 can be configured to send requests for imagery content from the client device 110 over the network 130 to server 120 and to receive content and messages sent to the client device 110 via the network 130. As described above, the imagery content can include still images as well as video content. For the collaborative method, network interface module 1210 can be configured to receive selection parameters set by a first user and transmit them over network 130 either to the server 120 for transfer to a second user's client device 110, or directly to the second user's client device 110. Network interface module 1210 on the second user's client device 110 can be further configured to transmit a request for selection parameters to server 120, and to receive selection parameters either from server 120 or the first user's client device.

Image management module 1220 is configured to receive a request for an image at a resolution and return the requested image at the requested resolution to the requestor. If the image is in data store 1250, the image management module 1220 retrieves the image from the data store 1250 rather than requesting the image from the server 120. If the requested image not in the data store 1250, the image management module 1220 sends a request to the network interface module 1210 to be transmitted to the server 120, and receives the image from the network interface module 1210 after the image is received from the server 120, and caches the image in the data store 1250. The image management module 1220 returns the image to the requesting module.

User interface module 1230 can be configured to accept user inputs from input device 1270 and display images (and other information) on display 1260 as illustrated in FIGS. 1 and 4. The user interface module can display a base-resolution image 150 and a virtual lens showing a high-resolution image 160 overlaid over the base-resolution image. According to some embodiments, the user interface module 1230 (and some or all of the other modules illustrated in FIG. 12) can comprise a plug-in, software library, service routine, function, process, thread, or device driver that can be executed or invoked by another program, such as a browser application or other application that can be executed on the client device 110. The user interface module 1230 can also input from one or more input devices 1270 such as buttons, keys, pointing devices or other input devices that allow a user to interact with the image viewing system. For example, the user interface module 110 can provide controls that allow a user to select the area of interest, size of the virtual lens and/or the resolution of the image displayed by the virtual lens.

The user interface module 1230 can also be configured to receive requests for a base-resolution or high-resolution imagery content from a user, and to instruct the request processing module 1240 to retrieve or generate the requested image, and display images received from the request processing module 1240 on display 1260. According to some embodiments, the user interface module 1230 can be configured to send requests to the request processing module 1240 for a base-resolution image, or to send a request to the request processing module 1240 for a composed image having a portion of a high-resolution image corresponding to an area of interest overlaid on the base resolution image at a location the corresponds to the area of interest. The user interface module 1230 displays the user-requested images received from the request processing module on display 1260. For the collaborative method, user interface module 1230 can send selection parameters set by a first user to the network interface module 1210 for transmission to the server 120 for a second user's retrieval, or to the second user's client device 110 either directly over the network or through transfer devices.

Request processing module 1240 can be configured to receive a request for an image from user interface module 1230. The request can be for a base-resolution image. In an embodiment, if selection parameters have been specified by a first user for a second user or generated by an algorithm for a second user, and the image request is from the second user, the request processing module 1240 can generate a composed image per the selection parameters. For a base-resolution image, when the successive download method or server composition method are used, the request processing module 1240 sends a request for the base-resolution image to the image management module 1220, and receives the base-resolution image from the image management module 1220. When the client downscaling method is used, the request processing module 1240 sends a request to the image management module 1220 for a top-resolution image, receives the top resolution image from the image management module 1220, and generates the base-resolution image from the top resolution image. The request processing module 1240 sends the base-resolution image requested by the user to the user interface module 1230 for display on display 1260. For a composed image, when the successive download method is used, the request processing module 1240 sends a request for the base-resolution image and the high-resolution image or portion of the high-resolution image corresponding to the area of interest to the image management module 1220. The request processing module 1240 receives the requested base-resolution image and high-resolution image from the image management module 1220. The request processing module 1240 then generates the user-requested composed image, with a portion of the high-resolution image corresponding to the area of interest overlaid on the base-resolution image at a location corresponding to the area of interest. When the client downscaling method is used, the request processing module 1240 requests a top-resolution image from the image management module 1220. Upon receiving the top-resolution image, the request processing module generates a base-resolution image and high-resolution image from the top-resolution image, and then generates the user-requested composed image, with a portion of the high-resolution image corresponding to the area of interest overlaid on the base-resolution image at a location corresponding to the area of interest. When the server composition method is used, the request processing module 1240 requests a composed image from the image management module 1220. The request processing module 1240 sends the composed image generated using any of these methods to the user interface module for display on display 1260.

For the collaborative method, request processing module 1240 on a second user's client device 110 can be configured to request selection parameters for an image from the network interface module 1210 set by a first user for the second user, and to receive the selection parameters from the network interface module 1210. The request processing module 1240 can also be configured to generate the selection parameters using algorithms. The request processing module 1240 can be configured to use the selection parameters to generate a composed image specified by the selection parameters, and send the composed image to the user interface module 1230 for display on display 1260. In generating the composed image, the request processing module can be configured to use either the successive download method, client downscaling method, or server composition method described above.

Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in computer or controller accessible on computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC. According to some embodiments, a software module can reside in a non-transitory computer-readable storage media.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

What is claimed is:

1. A computer-implemented method for displaying a portion of a higher-resolution image in the context of a lower-resolution image, wherein one or more processors are programmed to perform the steps comprising:
    sending a request to a server over a network for an image;
    receiving a lower-resolution image from the server over the network, wherein the lower-resolution image comprises the image at a first resolution;
    displaying the lower-resolution image on a display;
    receiving a user indication of a position that corresponds to a point in the lower-resolution image;
    sending a request to the server over the network for a composed image;
    receiving the composed image from the server over the network, wherein the composed image comprises the lower-resolution image and a virtual lens, wherein the virtual lens comprises a higher-resolution image, wherein the higher-resolution image comprises a portion of the image at a second resolution that is higher than the first resolution, and wherein the virtual lens is positioned on the lower-resolution image, such that, at the user-indicated position, a point in the higher-resolution image of the virtual lens matches the point in the underlying lower-resolution image; and
    replacing the lower-resolution image with the composed image on the display.

2. The method of claim 1 wherein the first resolution is less than a resolution of a maximum-resolution image generated on, input to, or stored on the server.

3. The method of claim 2 wherein the second resolution is less than or equal to the resolution of the maximum-resolution image.

4. The method of claim 2 wherein the first resolution is selected at least in part based on the capabilities of a client device or the network.

5. The method of claim 4 wherein the displayed lower-resolution image is generated from an image of greater than or equal resolution.

6. The method of claim 1 further comprising:
    receiving a request to resize the virtual lens;
    sending a request to the server for a second composed image with the virtual lens having the requested size;
    receiving the second composed image from the server; and
    displaying the second composed image on the display.

7. The method of claim 1 further comprising:
    receiving a request to change a shape of the virtual lens to a requested shape; and
    sending a request to the server for a second composed image with the virtual lens having the requested shape;
    receiving the second composed image from the server; and
    displaying the second composed image on the display.

8. The method of claim 1 further comprising:
    receiving a request to change a resolution of the higher-resolution image of the virtual lens;
    sending a request to the server for a second composed image;
    receiving the second composed image from the server, wherein the second composed image comprises the lower-resolution image and the virtual lens, wherein the virtual lens comprises a second higher-resolution image, wherein the second higher-resolution image comprises a portion of the image at a third resolution that is higher than the first resolution and different than the second resolution level, and wherein the virtual lens is positioned on the lower-resolution image, such that, at the user-indicated position, a point in the second higher-resolution image of the virtual lens matches the point in the underlying lower-resolution image; and
    displaying the second composed image on the display.

9. The method of claim 1, further comprising:
    tracking changes to the user-indicated position on the display;
    sending a request to the server for a second composed image;
    receiving the second composed image from the server, wherein the second composed image comprises the lower-resolution image and the virtual lens, wherein the virtual lens comprises a second higher-resolution image, wherein the second higher-resolution image comprises a portion of the image at the second resolution, and wherein the virtual lens is positioned on the lower-resolution image, such that, at the changed user-indicated position, a point in the second higher-resolution image of the virtual lens matches a point in the underlying lower-resolution image; and
    displaying the second composed image on the display.

10. The method of claim 1, further comprising displaying the lower-resolution image in response to a user command to hide the virtual lens.

11. The method of claim 10, further comprising displaying the composed image in response to a user command to show the previously hidden virtual lens.

12. The method of claim 1, wherein selections of a user are saved in a memory of a client device for later use.

13. A computer-implemented method for providing high-resolution imagery, wherein one or more processors are programmed to perform the steps comprising:
- receiving a request from a client device for an image at a first resolution;
- generating a lower-resolution image, wherein the lower-resolution image comprises the image at the first resolution;
- transmitting the lower-resolution image to the client device via a network;
- receiving a request for a composed image for a user-indicated position corresponding to a point in the lower-resolution image;
- generating the composed image, wherein the composed image comprises the lower-resolution image and a virtual lens, wherein the virtual lens comprises a higher-resolution image, wherein the higher-resolution image comprises a portion of the image at a second resolution that is higher than the first resolution, and wherein the virtual lens is positioned on the lower-resolution image, such that, at the user-indicated position, a point in the higher-resolution image of the virtual lens matches the point in the underlying lower-resolution image; and
- transmitting the composed image to the client device.

14. The method of claim 13 wherein the lower-resolution image is generated from the image, and wherein the image has a third resolution that is higher than the first resolution and higher than or equal to the second resolution.

15. The method of claim 13 wherein the higher-resolution image is generated from the image, and wherein the image has a third resolution that is higher than the first resolution and higher than or equal to the second resolution.

16. The method of claim 13, wherein the composed image further comprises a border around the higher-resolution image to demarcate the higher-resolution from the lower-resolution image.

17. The method of claim 13, wherein generating the composed image comprises rendering the virtual lens such that the virtual lens is centered over the user-indicated position.

18. The method of claim 17, wherein generating the composed image comprises:
- determining whether at least a portion of the virtual lens would be outside a border of the lower-resolution image if the virtual lens were rendered centered over the user-indicated position;
- if at least a portion of the virtual lens would not be outside a border of the lower-resolution image, rendering the virtual lens such that the virtual lens and the higher-resolution image are centered over the user-indicated position; and,
- if at least a portion of the virtual lens would be outside a border of the lower-resolution image, determining an offset location for the virtual lens where the virtual lens would not be outside of the border of the lower-resolution image, and rendering the virtual lens such that the virtual lens and the higher-resolution image are centered over the offset location.

19. The method of claim 13, further comprising adjusting the size, shape, or position of the virtual lens to improve the function of an application in which the virtual lens is being used.

20. The method of claim 13 wherein the image is video.

21. The method of claim 20, further comprising synchronizing a frame rate and a currently displayed frame of the higher-resolution image with a frame rate and currently displayed frame of the lower-resolution image.

22. The method of claim 13, wherein selections of the client device's user are saved in a memory of at least one server comprising the one or more processors for later use.

23. The method of claim 13 further comprising:
- verifying that the client device or a user of the client device has access rights to the lower-resolution image per an access control policy; and
- verifying that the client device or the user of the client device has access rights to the composed image per the access control policy.

24. A technical system for providing high-resolution imagery, the system comprising:
- at least one processor; and
- at least one module configured to, when executed by the at least one processor,
  - receive a request from a client device for an image at a first resolution,
  - generate a lower-resolution image, wherein the lower-resolution image comprises the image at the first resolution,
  - transmit the lower-resolution image to the client device via a network,
  - receive a request for a composed image for a user-indicated position corresponding to a point in the lower-resolution image,
  - generate the composed image, wherein the composed image comprises the lower-resolution image and a virtual lens, wherein the virtual lens comprises a higher-resolution image, wherein the higher-resolution image comprises a portion of the image at a second resolution that is higher than the first resolution, and wherein the virtual lens is positioned on the lower-resolution image, such that, at the user-indicated position, a point in the higher-resolution image of the virtual lens matches the point in the underlying lower-resolution image, and
  - transmitting the composed image to the client device.

25. The system of claim 24, wherein the at least one module is further configured to determine whether to transmit the lower-resolution image and the composed image to the client device based on one or more access rights for a user of the client device.

26. The system of claim 24, wherein the at least one module is further configured to generate the lower-resolution image based on the image, wherein the image has a third resolution that is higher than the first resolution and higher than or equal to the second resolution.

27. The system of claim 24, wherein the at least one module is further configured to generate the higher-resolution image based on the image, wherein the image has a third resolution that is higher than the first resolution and higher than or equal to the second resolution.

28. The system of claim 24, wherein the at least one module is further configured to:
- receive an image; and
- store the image in a data store.

29. The system of claim 24, wherein the at least one module is further configured to:
- generate the image; and
- store the image in a data store.

30. The system of claim 24, wherein the at least one module is further configured to:
- generate a plurality of images from the image, wherein the image has a third resolution, and wherein each of the plurality of images has a different resolution that is less than or equal to the third resolution; and
- store the plurality of images in a data store.

31. The system of claim 24, wherein the at least one module is further configured to store a set of user selections in a data store for later use.

32. The system of claim 24, wherein the at least one module is further configured to:
   verify that the client device or a user of the client device has access rights to the lower-resolution image per an access control policy; and
   verify that the client device or the user of the client device has access rights to the composed image per the access control policy.

33. A technical system for viewing high-resolution imagery, the system comprising:
   at least one processor; and
   at least one module configured to, when executed by the at least one processor,
      send a request to a server over a network for an image,
      receive a lower-resolution image from the server over the network, wherein the lower-resolution image comprises the image at a first resolution,
      display the lower-resolution image on a display,
      receive a user indication of a position that corresponds to a point in the lower-resolution image,
      send a request to the server over the network for a composed image,
      receive the composed image from the server over the network, wherein the composed image comprises the lower-resolution image and a virtual lens, wherein the virtual lens comprises a higher-resolution image, wherein the higher-resolution image comprises a portion of the image at a second resolution that is higher than the first resolution, and wherein the virtual lens is positioned on the lower-resolution image, such that, at the user-indicated position, a point in the higher-resolution image of the virtual lens matches the point in the underlying lower-resolution image, and
      replace the lower-resolution image with the composed image on the display.

34. The system of claim 33, wherein the at least one module is further configured to:
   check whether the lower-resolution image is cached in a data store; and
   retrieve the lower-resolution image from the data store if it is cached.

35. The system of claim 33, wherein the at least one module is further configured to cache one or more of the lower-resolution image and composed image in a data store.

36. The system of claim 33, wherein the at least one module is further configured to store a set of user selections in a data store for later use.

* * * * *